US008207091B2

(12) United States Patent
Stoller et al.

(10) Patent No.: US 8,207,091 B2
(45) Date of Patent: Jun. 26, 2012

(54) METHODS FOR IMPROVING GROWTH AND CROP PRODUCTIVITY OF PLANTS BY ADJUSTING PLANT HORMONE LEVELS, RATIOS AND/OR CO-FACTORS

(75) Inventors: Jerry H. Stoller, Bunker Hill Village, TX (US); Sherry Leclere, Pearland, TX (US); Albert Liptay, Houston, TX (US)

(73) Assignee: Stoller Enterprises, Inc., Houston, TX (US)

( * ) Notice: Subject to any disclaimer, the term of this patent is extended or adjusted under 35 U.S.C. 154(b) by 0 days.

(21) Appl. No.: 10/920,487

(22) Filed: Aug. 18, 2004

(65) Prior Publication Data

US 2005/0197253 A1 Sep. 8, 2005

(51) Int. Cl.
*A01N 43/36* (2006.01)
(52) U.S. Cl. ...................................... 504/138
(58) Field of Classification Search .................. None
See application file for complete search history.

(56) References Cited

U.S. PATENT DOCUMENTS

| 4,286,020 A | 8/1981 | Himel et al. |
| 4,496,388 A | 1/1985 | Clough |
| 4,675,327 A | 6/1987 | Fredrick |
| 4,755,397 A | 7/1988 | Eden et al. |
| 5,188,655 A | 2/1993 | Jones et al. |
| 6,361,999 B1 * | 3/2002 | Lin et al. ................. 435/410 |
| 6,399,646 B1 | 6/2002 | Riggle |
| 2005/0043177 A1 | 2/2005 | Stoller |
| 2005/0198896 A1 | 9/2005 | Quaghebeur |

FOREIGN PATENT DOCUMENTS

| AU | 716534 | 2/2000 |
| BR | PI9906202 | 9/2001 |
| CN | 1116044 | 2/1996 |
| CN | 1262037 | 8/2000 |
| CN | 1391807 | 1/2003 |
| DE | 4138209 | 5/1993 |
| DE | 4339198 | 5/1995 |
| DE | 19746366 | 5/1999 |
| EP | 0935918 | 8/1999 |
| GB | 1565906 | 1/1980 |
| JP | 51001209 | 1/1976 |
| JP | 57118503 | 7/1982 |
| JP | 07242590 | 9/1995 |
| JP | 95102367.5 | 2/1996 |
| JP | 2002262687 | 9/2002 |
| JP | 02117261.7 | 1/2003 |
| WO | 87/03780 | 7/1987 |
| WO | 91/18512 | 12/1991 |
| WO | 94/00986 | 1/1994 |
| WO | 95/03702 | 2/1995 |
| WO | 96/28026 | 9/1996 |
| WO | 98/00023 | 1/1998 |
| WO | 99/49728 | 10/1999 |
| WO | WO 0005954 | * 2/2000 |
| WO | 03/096806 | 11/2003 |
| WO | 2005/018319 A2 | 3/2005 |

OTHER PUBLICATIONS

Coenen et al. "Auxin-cytokin interactions in higher plants: old problems and new tools". Trends in Plant Science. 2(9):351-356. Sep. 1997.*
Mohr et al. "Physiology of Hormone Action", Chapter 23 in Plant Physiology. Springer. p. 383-408. 1995.*
Bernier et al. "Physiological Signals That Induce Flowering". The Plant Cell. 5:1147-1155. Oct. 1993.*
Ono et al (Interactions between auxins and boric acid in the rooting of stem cuttings of *Coffea arabica* L. CV. Mundo Novo, Scientia Agricola (Piracicaba, Brazil), 1992, 49 (Numero Espec.), 23-7). ABS.*
Trifu et al (The effect of the complex treatment with cobalt-60 emitted gamma rays, beta indoleacetic acid and boron on RNA. dynamics in corn, Contributii Botanice, 1977, 183-9). ABS.*
Nath et al (Propagation of certain bamboo species from chemically treated culm cuttings, Indian Journal of Fosrestry, 1986, vol. 9 No. 2, pp. 151-156). ABS.*
Ono et al (Interactions between auxins and boric acid in the rooting of stem cuttings of *Coffea arabica* L. CV. Mundo Novo, Scientia Agricola (Piracicaba, Brazil), 1992, 49 (Numero Espec.), 23-7).*
Trifu et al (The effect of the complex treatment with cobalt-60 emitted gamma rays, beta indoleacetic acid (IAA)and boron on RNA dynamics in corn, Contributii Botanice, 1977, 183-9).*
Nath et al (Propagation of certain bamboo species from chemically treated culm cuttings, Indian Journal of Fosrestry, 1986, vol. 9 No. 2, pp. 151-156).*
Coenen et al. (Trends in Plant Science, vol. 2 No. 9, 351-356).*
Johri, M.M., and Doyel Mitra. "Action of Plant Hormones." Current Science. vol. 80, No. 2 (Jan. 25, 2001) pp. 199-205. Kende, Hans, and Jans A.D. Zeevaart. "The Five "Classical" Plant Hormones." Plant Cell. American Society of Plant Physiologists. vol. 9. (Jul. 1997) pp. 1197-1210.
Torrey, John G., "Root Hormones and Plant Growth." Annual Review of Plant Physiology. vol. 27, (1976) pp. 435-459.
English machine translation of JP 02117261.7 (Xuanguo et al.), Jan. 22, 2003.
English machine translation of JP 95102367.5 (Fashui et al.), Feb. 7, 1996.

(Continued)

*Primary Examiner* — Alton Pryor
(74) *Attorney, Agent, or Firm* — Gary L. Bush; Andrews Kurth LLP

(57) ABSTRACT

In agriculture when temperature and moisture deviate from the norm two things happen, plant growth suffers and disease flourishes. The Stoller model for plant growth states that proper hormone balance is necessary for optimum growth and performance. When growth conditions deviate from the norm, hormone balance is altered and plant growth suffers. This invention presents evidence to support this model and explain the relationship between hormone levels and plant growth. A clear understanding of this relationship will facilitate crop treatments aimed to eliminate these problems. Although we cannot control the climate, we can control the damage caused by environmental stresses by manipulating the levels and/or ratio of plant hormones in the different plant tissues. By adjusting the levels and/or ratios of hormones, particularly auxin and cytokinins in the root tissue, we can assist the plant in overcoming or compensating for this environmental stress.

16 Claims, 18 Drawing Sheets

OTHER PUBLICATIONS

Kirillova, I.G. et al. "Effects of Ambiol and 2-chlorethylphosphonic Acid on the Contents of Phytohormones in Potato Leaves and Tubers." Mar. 2003. Prikladnaya Biokhimiya I Mikrobiologiya, vol. 39, No. 2, pp. 211-214.

Romanov, G.A. et al. "Effect of Indole-3-acetic Acid and Kinetin on Tuberisation Paramaters of Different Cultivars and Transgenic Lines of Potato in Vitro." Plant Growth Regulation, vol. 32, No. 2-3, Nov. 2000, pp. 245-251.

European Search Report of Corresponding Application No. 04786531.6 dated Mar. 19, 2010.

International Preliminary Report on Patentability for PCT/US04/26700, dated Jun. 16, 2006.

Written Opinion of the International Searching Authority for PCT/US04/26700, dated Jan. 4, 2006.

International Search Report for PCT/US04/26700, dated Jan. 4, 2006.

International Preliminary Report on Patentability for PCT/US04/26851, dated Jun. 16, 2006.

Written Opinion of the International Searching Authority for PCT/US04/26851, dated Dec. 12, 2005.

International Search Report for PCT/US04/26851, dated Dec. 12, 2005.

U.S. Appl. No. 10/677,708, filed Oct. 2, 2003.

Jarvis, B. C. et al. "Auxin and Boron in Relation to the Rooting Response and Ageing of Mung Bean Cuttings." New Phytologist (1983), vol. 95, pp. 509-518.

Jarvis, B. C. et al. "The Interaction Between Auxin and Boron in Adventitious Root Development." New Phytologist (1984), vol. 97, pp. 197-204.

Colombian Office Action for counterpart patent application No. 06-27206 as issued by the Colombian Patent Office on Oct. 8, 2010.

English translation of Colombian Office for counterpart patent application No. 06-27206 as issued by the Colombian Patent Office on Oct. 8, 2010.

European Supplementary Search Report of application No. 04781404.1 dated Mar. 31, 2010.

English translation of BR PI9906202 in the Name of Unicamp Universidade Estadual de Campinas Unicamp.

English translation of CN 1116044 in the Name of Huaibei Coal Normal College.

English translation of CN 1262037 in the Name of Wei Hongru.

English translation of CN 1391807 in the Name of Sichuan Lomon Fusheng Technology Co., Ltd.

English translation of DE 19746366 in the Name of Temmen GmbH.

English translation of DE 4138209 in the Name of Seifert, et al.

English translation of DE 4339198 in the Name of Max Planck Gesellschaft.

English translation of JP 51001209 in the Name of Sasano.

English translation of JP 57118503 in the Name of Sumitomo Chemical Co.

English translation of JP 07242590 in the Name of Sumitomo Chemcial Co.

English translation of JP 2002262687 in the Name of Nettai Rin Saisei Gijutsu Kenkyu Kumiai.

English translation of WO 95/03702 in the Name of Consejo Superior Investigaciones Cientificas.

Ogbonna, et al. "Effect of Seed-pretreatment With Some Plant Growth Regulators on Germination, Growth and Yield of Cowpea." Nippon Sakumotsu Gakkai Kiji, 1989, 58(4), 641-47.

Prasad, et al. "Physio Therapy of Rice Plant Against the Root-knot Nematode Meloidogyne-graminicola." Biological Sciences, 1976, vol. 42, No. 6, pp. 295-298.

Cohen, et al. "Local and Systemic Protection Against Phytophthora Inestans Induced in Potato and Tomato Plants by Jasmonic Acid and Jasmonic Methyl Ester." Phytopathology, St. Paul, MN vol. 83, No. 10 Jan. 1, 1993, pp. 1054-1062.

Penninckx, et al. "Pathogen-Induced Systemic Activation of a Plant Defensin Gene in Arabidopsis Follows a Salicylic Acid-Independent Pathway." American Society of Plant Physiologists, Rockville, MD vol. 8, No. 12, Dec. 1, 1006, pp. 2309-2323.

Xu, et al. "Plant Defense Genes are Synergistically Induced by Ethylene and Methyl Jasmonate." The Plant Cell, American Society of Plant Physiologists, Rockville, MD. vol. 6, No. 8. Aug. 1, 1994, pp. 1077-1085.

Ono, E.O., Niimachi, Pilott, J.D., and Pinho, S.Z "Interaction Between Auxins and Boric Acid in Rooting of Stem Cuttings of *Coffee arabica*L. CV New world." Scientia Agricol [Piracicaba, Brazil], 1992, vol. 49 (Numero Espec.). [Apparant English Equivalent of Ono, E.O., et al cited in Nov. 1, 2007 Office Action and Jan. 26, 2010 Final Rejection].

Ono, et al. "Interaction Between Auxins and Boron in the Rooting of Camellia Japonica Cuttings." Revista Brasileira de Fisiologia Vegetal. 1992, vol. 4(2):107-112. [with English Abstract].

* cited by examiner

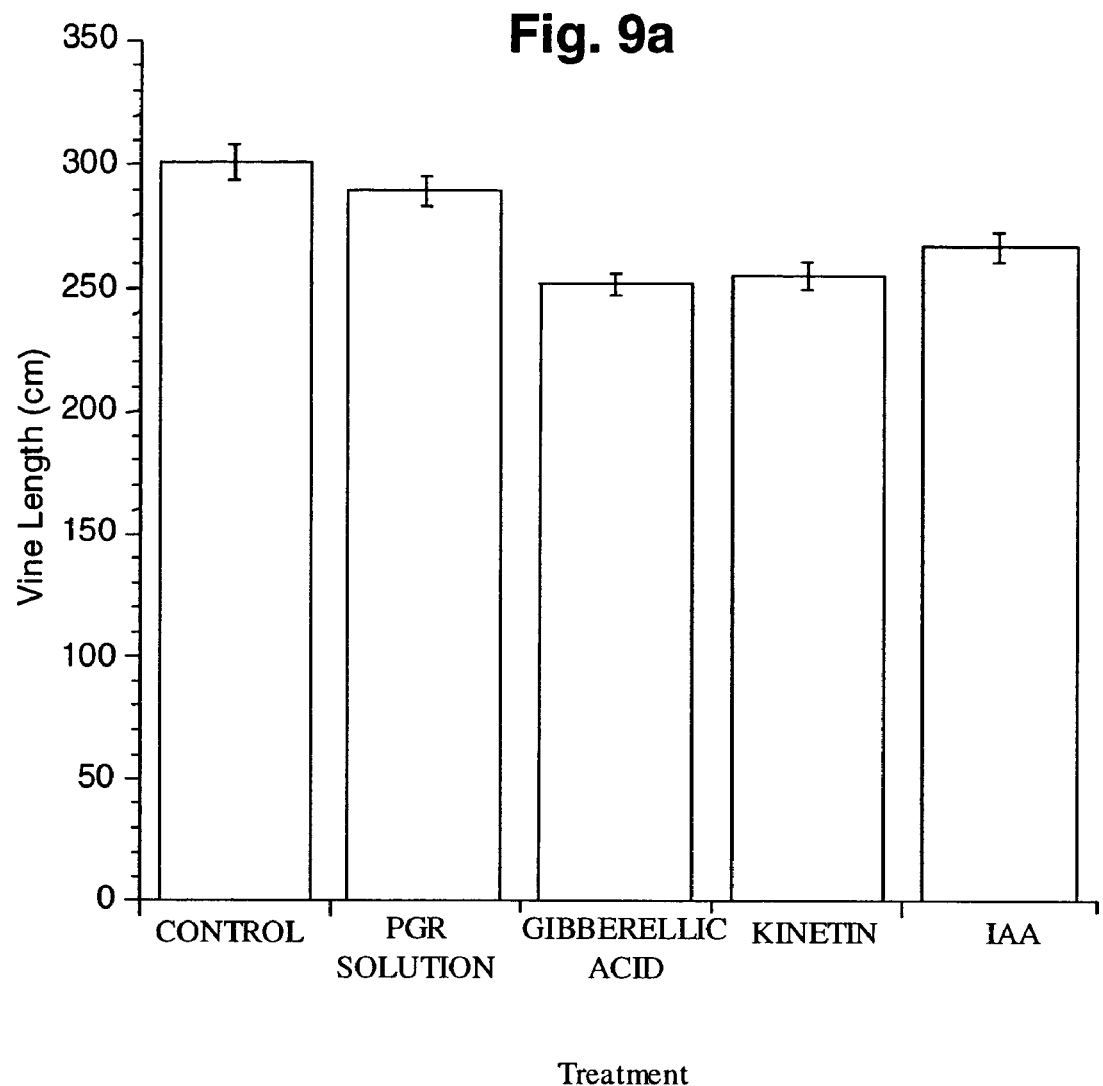

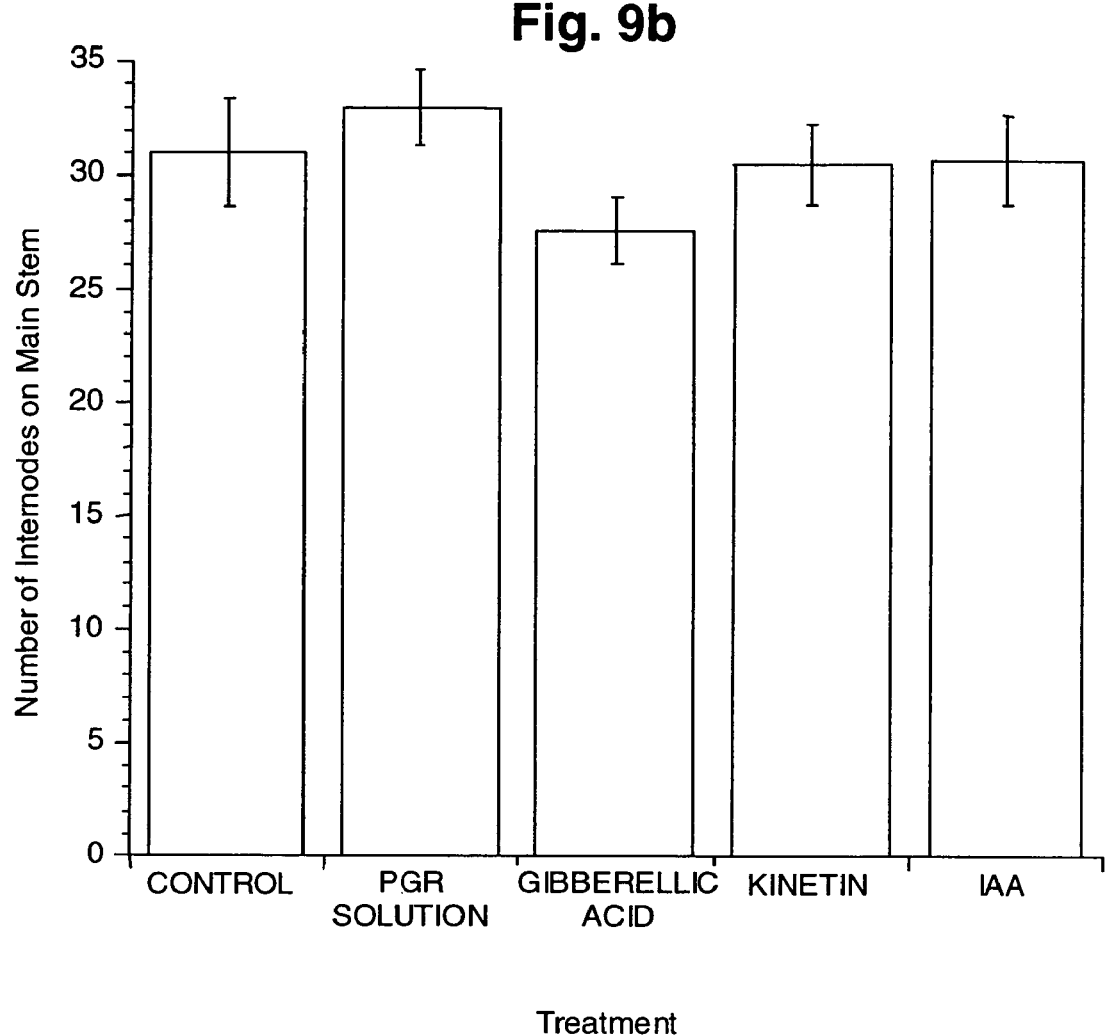

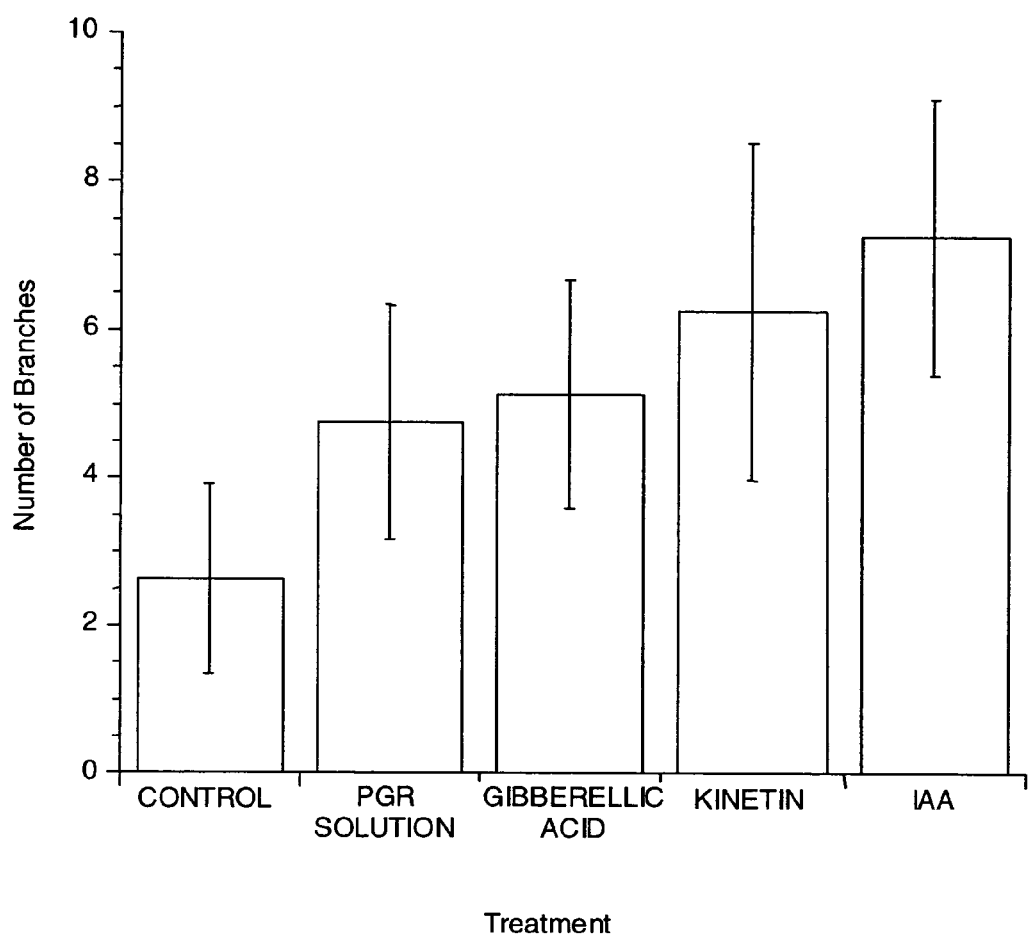

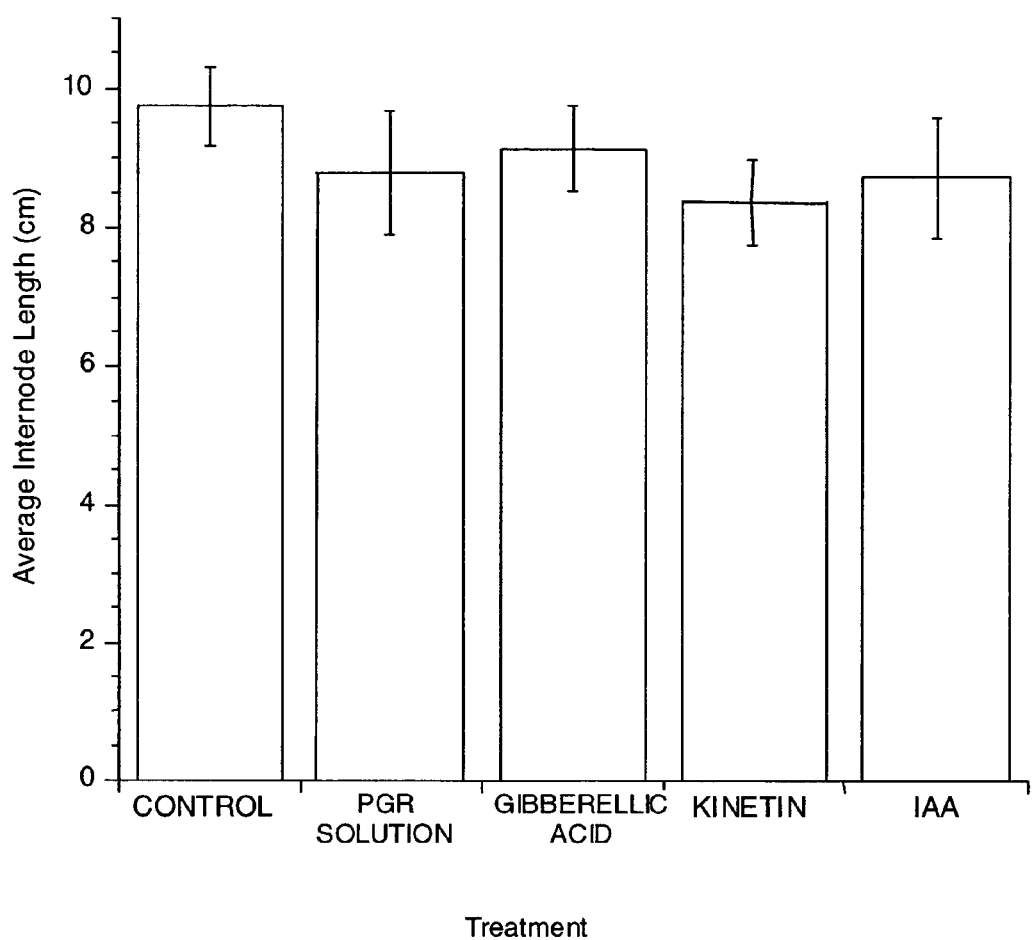

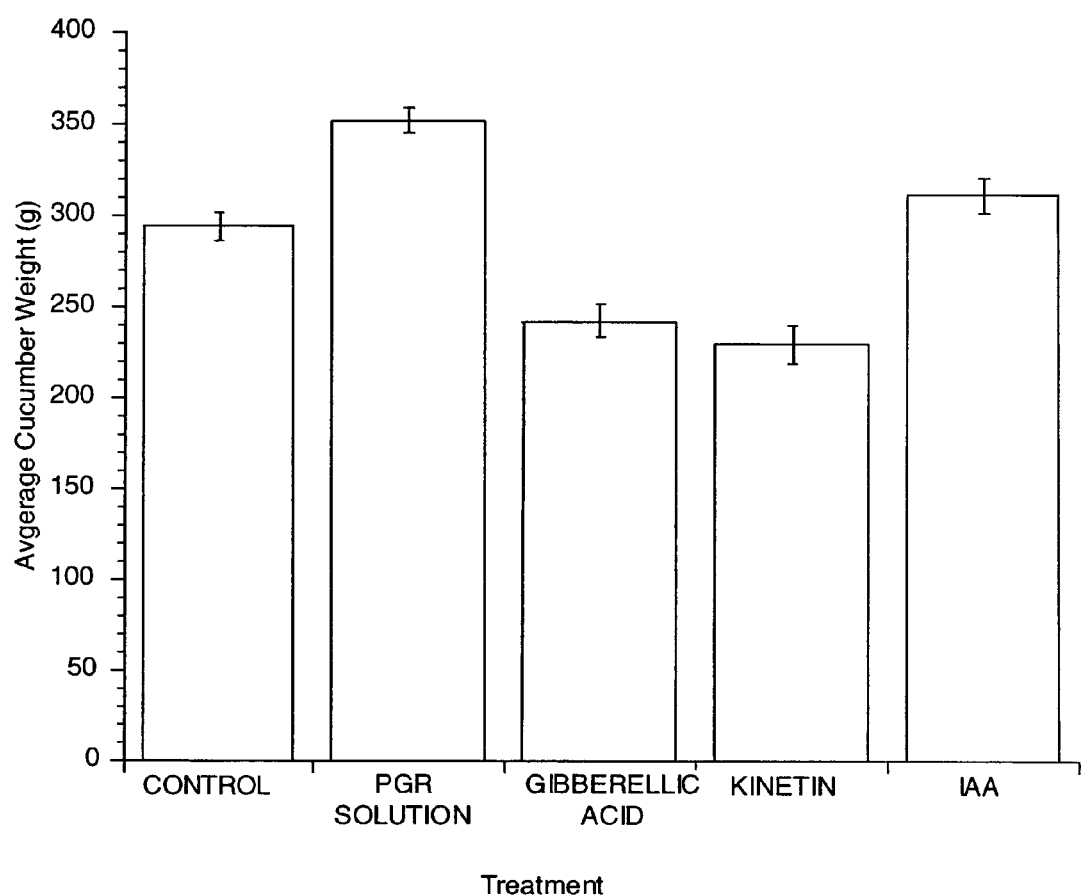

METHODS FOR IMPROVING GROWTH AND CROP PRODUCTIVITY OF PLANTS BY ADJUSTING PLANT HORMONE LEVELS, RATIOS AND/OR CO-FACTORS

BACKGROUND OF THE INVENTION

I. Field of the Invention

The present invention generally relates to methods for improving the growth and crop productivity of plants by adjusting plant hormone levels and/or ratios. These methods are also useful for improving the resistance of plants to infestation by insects and pathogens, while, at the same time, improving plant growth by controlling plant hormones. More specifically, the present invention is directed to methods for achieving those goals by applying an effective amount of one or more plant hormones to the plant tissue. Alternatively, these goals are achieved by applying to the plant tissue other substances that effect the level of one or more plant hormones in the plant tissue, causing the hormone(s) to move into a desired range.

II. Description of the Background

Plant hormones have been known and studied for years. Plant hormones may be assigned to one of five categories: auxins, cytokinins, gibberellins, abscisic acid and ethylene. Ethylene has long been associated with fruit ripening and leaf abscission. Abscisic acid causes the formation of winter buds, triggers seed dormancy, controls the opening and closing of stomata and induces leaf senescence. Gibberellins, primarily gibberellic acid, are involved in breaking dormancy in seeds and in the stimulation of cell elongation in stems. Gibberellins are also known to cause dwarf plants to elongate to normal size. Cytokinins, e.g., zeatin, are produced primarily in the roots of plants. Cytokinins stimulate growth of lateral buds lower on the stem, promote cell division and leaf expansion and retard plant aging. Cytokinins also enhance auxin levels by creating new growth from meristematic tissues in which auxins are synthesized. Auxins, primarily indole-3-acetic acid (IAA) promote both cell division and cell elongation, and maintain apical dominance. Auxins also stimulate secondary growth in the vascular cambium, induce the formation of adventitious roots and promote fruit growth.

Auxins and cytokinins have complex interactions. It is known that the ratio of auxin to cytokinin will control the differentiation of cells in tissue cultures. Auxin is synthesized in the shoot apex, while cytokinin is synthesized mostly in the root apex. Thus, the ratio of auxin to cytokinin is normally high in the shoots, while it is low in the roots. If the ratio of auxin to cytokinin is altered by increasing the relative amount of auxin, root growth is stimulated. On the other hand, if the ratio of auxin to cytokinin is altered by increasing the relative amount of cytokinin, shoot growth is stimulated.

The most common naturally occurring auxin is indole-3-acetic acid (IAA). However, other synthetic auxins, including indole-3-butyric acid (IBA); naphthalene acetic acid (NAA); 2,4-dichlorophenoxy acetic acid (2,4-D); and 2,4,5-trichlorophenoxy acetic acid (2,4,5-T or agent orange) are known. While these are recognized as synthetic auxins, it should be acknowledged that IBA does naturally occur in plant tissues. Many of these synthetic auxins have been employed for decades as herbicides, producing accelerated and exaggerated plant growth followed by plant death. Agent orange gained widespread recognition when it was used extensively by the United States Army and Air Force in deforestation applications during the Vietnam War. 2,4-D finds continuing use in a number of commercial herbicides sold for use by the home gardener.

Compounds are classified as auxins based on their biological activity in plants. A primary activity for classification includes simulation of cell growth and elongation. Auxins have been studied since the 1800's. Charles Darwin noticed that grass coleoptiles would grow toward a uni-directional light source. He discovered that the growth response of bending toward the light source occurred in the growth zone below the plant tip, even though it was the tip that perceived the light stimulus. Darwin suggested that a chemical messenger was transported between the plant tip and the growth zone. That messenger was later identified as an auxin.

All plants require a certain ratio of auxin, i.e., IAA, to cytokinin for cell division. While the ratios may vary, it is well known that the ratio of IAA to cytokinin must be much greater for cell division in the apical meristem tissue than the ratio in the meristem tissue of the roots. Each part of a plant may require a different IAA to cytokinin ratio for cell division. For example, different ratios may be required for cell division in the stem, fruit, grain and other plant parts. In fact, it has been estimated that the ratio for apical meristem cell division may be considerably more, in fact, as much as 1000 times greater than the ratio necessary for root cell division. While the mechanism by which this ratio is determined remains unknown, other hormones and enzymes are likely to be involved in its perception.

Plants generally grow best at temperatures from about 68° F. to about 87° F. (about 21-30° C.). In this temperature range it is presumed that plants produce sufficient amounts of auxins, particularly IAA, to maintain normal growth. While ideal temperatures vary among species, crop plants typically grow best in the foregoing range. While temperature is an important factor, it should also be noted that other environmental factors can effect cell division. The moisture content of the plant, the nutrient status (especially the level of available nitrogen), the light intensity on the plant and the age of the plant, together with the temperature, all effect the ability of the plant to produce plant hormones, including IAA and cytokinin which dictate cell division.

As the temperature rises above about 90° F. (above about 31° C.) or falls below about 68° F. (21° C.) plant growth and cell division slow. As the temperature further increases above about 90° F. and drops below about 68° F., the production of IAA and other plant hormones decreases at an accelerating rate. Thus, it becomes difficult, if not impossible, to achieve new cell growth at temperatures above about 100° F. Similarly cell division slows and then ceases as temperatures plunge significantly below about 68° F. During normal growing conditions with adequate moisture and temperature, i.e., temperatures between about 70° F. and 90° F., the plants will produce an abundance of IAA. Cell division may be further impeded by other inhibitive compounds produced by IAA and other plant hormones. As temperatures increase above about 90° F. or below about 68° F., the ability of plants to produce IAA rapidly diminishes.

Plants respond to light during the growth process. The light in the range of the red wavelengths is primarily used by plants in order to trigger normal plant growth. It also determines the plant's photoperiodism. When plants are spaced at relatively high density in a field, red wavelength light is reduced on plant parts by the shading effect of neighboring plants. This causes the shaded plant to seek out more sunlight and causes the extension of internode length as the shaded plant rapidly grows to seek more sunlight. It is well known that auxin (particularly IAA) moves from the light side of plant tissue to the dark side. When shading of lower plant parts becomes prominent in a field of plants, the movement of IAA from the new apical meristem tissue rapidly accelerates downward in the plant. The movement of IAA downward will be dependent upon the amount of shade that occurs at the bottom of the plant.

Since gibberellic acid tends to migrate in a plant to where there is the most abundance of red wavelength light, it will tend to move upward in a plant toward the apical meristem tissue. This, in turn, triggers the more rapid movement downward of IAA toward the shaded side of the plant. The amount of movement of IAA downward will depend upon the positioning of the apical meristem tissue of the plant. If the apical meristem tissue is located more vertically from the plant crown, IAA movement downward will be greater. If the apical meristem tissue is located more horizontally relative to the plant crown, IAA movement will be less. If the apical meristem tissue on a branch or a limb is bent downward, it is very difficult for IAA to move against gravity and therefore its movement downward will be limited.

When plants are rapidly growing under conditions that include ample moisture, ideal temperatures and ample amounts of nitrogen fertilizer, auxins are efficiently transported out of the tissues where they are metabolized and move downward in the plant. This results in the redistribution of auxin and the reduction of the auxin level in the tissues where it was produced. The result is tissues that are deficient in the level of auxin.

The present invention is based upon the Stoller model for plant growth. This model was developed from a combination of field observations and analysis of the scientific literature. This model takes into account published data on plant hormone levels and relates them to plant growth that can be observed to result from changes in these hormone levels. Although much research has been done over the past century on plant hormones, this is to our knowledge the first comprehensive model relating levels of hormones directly to field-observed plant growth responses. This model also provides for the first time an applicable method for controlling plant growth in the field with natural plant hormones to generate desired growth. Although there is a broad research base in the literature, most of this research deals with only one hormone or the specifics of the interaction of a subset of hormones within a very defined event. In addition most of this published work has been done in the laboratory on model plants, or has been done in vitro in excised or disrupted plant tissues. Never before has a model been published that relates the wide array of hormone responses to one another within developmental events with an eye to altering these responses to affect crop production by generating more ideal growth.

Ideal plant growth is defined as growth that would occur under conditions of ideal temperature, moisture, light, and nutrient balance, and is represented by adequate growth of both root and shoot tissues such that the growth of one tissue does not dominate at the expense of another tissue during any growth stage. During ideal growth a plant is neither infected by pathogens nor invaded by insects or parasites. An ideally growing plant is generally compact in appearance, with equal amounts of root and shoot mass, good color, and good flower and fruit set. An ideally growing plant will give the maximum yield possible from its genetic potential.

There is a remarkable uniformity of boron requirements and/or boron deficiency symptoms across plant and crop species. The youngest growing tissues are always affected first and in all cases root growth is rapidly impaired. These are the tissues in plants whose regulation and development is also controlled largely by plant hormones. Boron should extend the life and, therefore, the effectiveness of IAA by reducing the breakdown of IAA by IAA-oxidase. Boron has also been shown to increase polyamines, putrescine, spermidine, ascorbic acid, spermine, and the plant hormones, IAA and gibberellic acid. Thus, there is an important interaction/enhancement or synergism between hormones, especially auxin, and boron and other minerals in physiological activity. For example, boron appears to have a direct effect on transport of the plant hormone auxin, possibly by the movement of auxin in and out of cells.

Boron has been shown to be essential for nitrogen fixation by plants, where it enhances the stability of the interconnections between the nodules and the plant roots. Moreover, from an evolutionary standpoint boron-regulated growth may be correlated with the ability of vascular plants to maintain upright growth and to form lignified secondary walls.

Boron deficiency and toxicity inhibit ATPase-dependent hydrogen pumping and ATPase activity in sunflower roots and elicit proton leakage from cells. Thus, membrane activity is strengthened with sufficient and appropriate boron levels through more effective ATPase activity and controlled conductance across the plasma membrane. Borate compounds can inhibit calcium-stimulated ATPase activity as well as store-operated calcium entry channels. Boron enhances phosphorylation and, therefore, signals transduction, including hormone transduction, probably through a mediator whose transduction signals involve a cascade of phosphorylations. It has been reported that boron deficiency reduces oxidative damage to cells and that ascorbate and glutathione levels decrease dramatically with boron deficiency. It has also been suggested that the oxidative damage from boron deficiency is the result of impaired cell wall structure.

Through its effect on proton secretion and on the activity of the plasma membrane NADH oxidase, boron may be directly associated with cell growth. An aploplastic target for the primary action of boron deprivation which signals deeper into the cell via endocytosis-mediated pectin along a putative cell wall plasma membrane cytoskeleton continuum has also been suggested. Boron in animals can act both at the transcriptional and translational level. Further research will likely bear out similar action in plants. Boron is taken up by the plant and accumulates at the growing points where it enters the cell walls. Ninety (90) percent of boron in a plant is in the cell walls in the pectin fraction referred to as the rhamnogalacturonan region where it may be involved in cell to cell adhesion and therefore cell signaling for effective plant growth. Pollen germination is especially sensitive to boron deficiency. It has been suggested that boron has an important role in ionic membrane transport regulation. Boron appears to be most active in the G2/M phase of the cell cycle, i.e., just before and during mitosis when cells divide.

Further derivatives of boron have been reported to have anti-fungal and anti-bacterial activities. Those activities may be strengthened in combination with plant growth regulators, in particular auxin.

Those skilled in the art have longed sought environmentally friendly methods for improving plant growth and crop productivity while also improving the resistance of plants to pathogens and insects. Thus, there has been a long felt, but unfulfilled need, for such methods. The present invention solves those needs.

SUMMARY OF THE INVENTION

This invention provides a model for understanding the ways hormones function in crop plants, and provides methods by which plant growth can be manipulated through the addition of hormone solutions through application to roots or aerial tissues. The method relies on the observation that the root of the plant is the primary organ responsible for sensing environmental conditions and sending hormone cues. Central to the invention is the observation that hormone responses are determined chiefly by the establishment of auxin and cytokinin gradients within the plant. It is the relative levels of hormones to one another and to auxin and cytokinin that are the determining factors for most hormone responses. By altering the hormone ratios within tissues through the application of one or more plant growth regulators, preferably auxin and/or cytokinin, we can alter plant growth responses.

The present invention is directed to methods for improving the growth and crop productivity of plants by adjusting the level or ratio of plant hormones in the tissues of the plant. In the methods of the present invention, a plant hormone in an amount effective to produce the desired effect, e.g., improved growth, improved fruit set, or improved plant architecture, is applied to the plant tissue. Improvements to plant architecture may include more prolific and continuous root growth; shorter stature with shorter internodes; stalkier, more branching shoot configuration; thicker leaves with enhanced photosynthetic capacity and enhanced sugar (photosynthate) transfer to the anatomic, crop portions having economic interest to the producer; even, continuous and enhanced cell division and cell expansion resulting in improved number and quality of flower pollination, fruit initiation, fruit sizing and compositional development; or similarly, enhanced tuber, seed, stem or leaf development and performance with concomitant enhanced qualities in shipping, storage or merchandising. While any of the plant hormones may be effective, the hormone is typically selected from the auxins, cytokinins, gibberellins and abscisic acid. The presently preferred hormone is an auxin, particularly indole-3-acetic acid (IAA) or indole-3-butyric acid (IBA). However, the auxin is applied in an amount insufficient to negatively affect growth of the plant tissues. Alternatively, other plant growth regulators (PGRs), which act by altering the level, ratio or effectiveness of endogenous or applied hormones, may be used.

The auxin is selected from the group consisting of the natural auxins, synthetic auxins, auxin metabolites, auxin precursors, auxin derivatives and mixtures thereof. The preferred auxin is a natural auxin, most preferably indole-3-acetic acid. The presently preferred synthetic auxin is indole-3-butyric acid. Alternatively, manipulation of the auxin level within the desired range can be achieved by application of a plant growth regulator or hormone, e.g., cytokinin or gibberellic acid.

In the methods of the present invention, a hormone, e.g., an auxin or another PGR, is applied to the seed or tubers of the plant prior to planting. Alternatively, the auxin or PGR is applied to the roots, foliage, flowers or fruits of the plant after planting. When applied to the seed or tubers, auxin is preferably applied at a rate of about 0.0028 to about 0.028 grams auxin per 100 kg. seed weight. When applied to potato seed pieces, the rate of application may be calculated so as to result in about 0.0125 to about 2.8 grams auxin per hectare of planted pieces. When applied to the roots, foliage, flowers or fruits of plants, the auxin should be applied at a rate of about 0.0002 to about 0.06 grams auxin per hectare per day. Multiple applications may be required over an extended growing period.

The hormone, e.g., an auxin or another PGR, may be applied as an aqueous solution or as a powder. When applied as an aqueous solution, the solution may be applied to the plant tissue by conventional spraying or irrigation techniques. The solution may further include a metal selected from the group consisting of the alkaline earth metals, transition metals, boron and mixtures thereof. Such metals preferably are selected from the group consisting of calcium, magnesium, zinc, copper, manganese, boron, iron, cobalt, molybdenum and mixtures thereof. Seeds or tubers may be treated prior to planting by spraying with or by immersion in such aqueous solutions. The preferred method of applying PGRs may be along with a boron-containing solution. Boron will stabilize the auxin in plant tissues to which such solutions are applied.

The application of a metal, preferably boron, together with the PGR appears to extend the effective life of the PGR, thus permitting longer times between repeat applications. Boron appears to improve the efficacy, both the life and activity, of added IAA by suppressing the activity and or synthesis of IAA-oxidase, the enzyme that degrades IAA in plants. The anti-oxidant ascorbic acid may be part of the mechanism through which boron enhances IAA activity. Boron also enhances sugar transport in plants, cell wall synthesis, lignification, cell wall structure through its borate ester linkages, RNA metabolism, DNA synthesis, phenol metabolism, membrane functions and IAA metabolism. Further, boron is known to modulate respiration. The boron requirement for reproductive growth is higher than that for vegetative growth. Boron interacts with auxin especially in cell elongation such as pollen tubes, trichomes and other cells. Boron also stimulates auxin-sensitive plasmalemma NADH-oxidase and is necessary for the auxin stimulation of ferricyanide-induced proton release in plant cells. Boron is also part of the endocytosis mechanism of rhamnogalacturonan II dimers (linking through di-ester bonds) in formation of primary walls in dividing cells such as root tips, trichomes or pollen tubes. Thus, boron is linked with auxin-mediated cell division as well as auxin-mediated cell elongation. Finally, boron has been reported to have anti-fungal and anti-bacterial activities. Accordingly, it is believed that application of PGRs, together with boron, will improve the effect of the PGR in suppressing insect and pathogen infestation in plants.

The hormone, e.g., an auxin or other PGRs, may also be applied as a dry powder. In such applications, the hormone is mixed with an environmentally and biologically compatible material. The powder may be applied to the foliage, flowers or fruits of the plant by conventional dusting methods. Alternatively, the powder may be encapsulated in a biologically compatible material to provide slow release when placed on or near the seeds, tubers or roots of the plant. Exemplary biologically compatible materials include the clays, lignites, resins, silicones and mixtures thereof.

The methods of the present invention improve plant architecture, e.g., by limiting excessive growth of vines, by controlling internode length, by controlling top growth, by controlling flower set, by increasing fruit size and/or by increasing total crop yield. These improvements are achieved by applying an effective amount of a hormone, preferably an auxin, to the plant tissue.

Finally, the present invention includes seeds and seed pieces for producing plants having dispersed on the surface thereof a hormone, e.g., an auxin or other PGR, in an amount effective to alter plant architecture as explained above, but in an amount insufficient to negatively effect growth of the plant tissues. Alternatively, a plant growth regulator, e.g., a plant hormone such as cytokinin or gibberellic acid, which acts by affecting the level or effectiveness of applied auxin may be used. Such PGR should be dispersed on the surface of seeds or seed pieces in an amount effective to manipulate the auxin level within the desired range.

The methods of the present invention have been found to improve the growth and productivity of plants by altering plant architecture as explained above. Significantly, these improvements have been achieved without the use of environmentally hazardous chemicals. The methods to the present invention achieve these improvements by applying naturally occurring or synthetic plant hormones to adjust the hormone levels and ratios within the plant tissues to produce the desired results. Thus, the long felt, but unfulfilled need for environmentally friendly methods for enhancing plant growth and productivity have been met. These and other meritorious features and advantages of the present invention will be more fully appreciated from the following detailed description and claims.

BRIEF DESCRIPTION OF THE DRAWINGS

Other features and intended advantages of the present invention will be more readily apparent by reference to the following description in connection with the accompanying drawings wherein:

FIGS. 9a-9e are bar graphs illustrating, respectively, the average vine length, average internode number, average number of branches, average internode length and average fruit length of cucumber plants treated with various plant hormones in accord with the present invention as summarized in Table V;

While the invention will be described in connection with the presently preferred embodiments, it will be understood that it is not intended to limit the invention to those embodiments. To the contrary, it is intended to cover all alternatives, modifications and equivalents as may be included in the spirit of the invention as defined in the independent claims.

DETAILED DESCRIPTION OF THE INVENTION

Plant Hormones During Development

The Stoller model for plant growth states that plant growth is a direct response to hormone signals and hormone balance, and this balance is dynamic, changing with plant age and in response to environmental conditions such as temperature, moisture, nutrient balance, and light. Early in seed formation, cytokinin levels briefly rise to a maximum level, and this rise coincides with a period of rapid cell division (Lur and Setter 1993). This is followed by a rise in auxin, gibberellin and abscisic acid levels (Marschner 1986). In the beginning stages of plant growth following seed inhibition, cytokinin is the first hormone produced. This is perhaps most obvious through the observation that during seed germination, the radicle, or seedling root, is the first structure to emerge from the seed coat. The root is the primary site of cytokinin biosynthesis (Davies 1995). Cytokinin then moves from the root tip upward into the shoot, and establishes a gradient in which cytokinin is high in root tips and decreases gradually toward the shoot apex. Once cytokinin has reached the shoot apex, cell division is stimulated. These new shoot tissues produce auxin, and this auxin is the dominant hormone in young shoot tissues (Davies 1995). During this stage, cell division and therefore growth is directly correlated to the relative amounts of auxin and cytokinin in the tissue, as the length of time cell division will occur is dependent on the relative amounts of these hormones. When levels in the tissue are adequate, cell division will occur. When levels of one or both of these hormones decrease below a critical ratio, cell division will cease. If hormones can be added to tissues at this time, the period of cell division can be prolonged. This will potentially increase cell number and, therefore, size of plant tissues.

Figure 1:
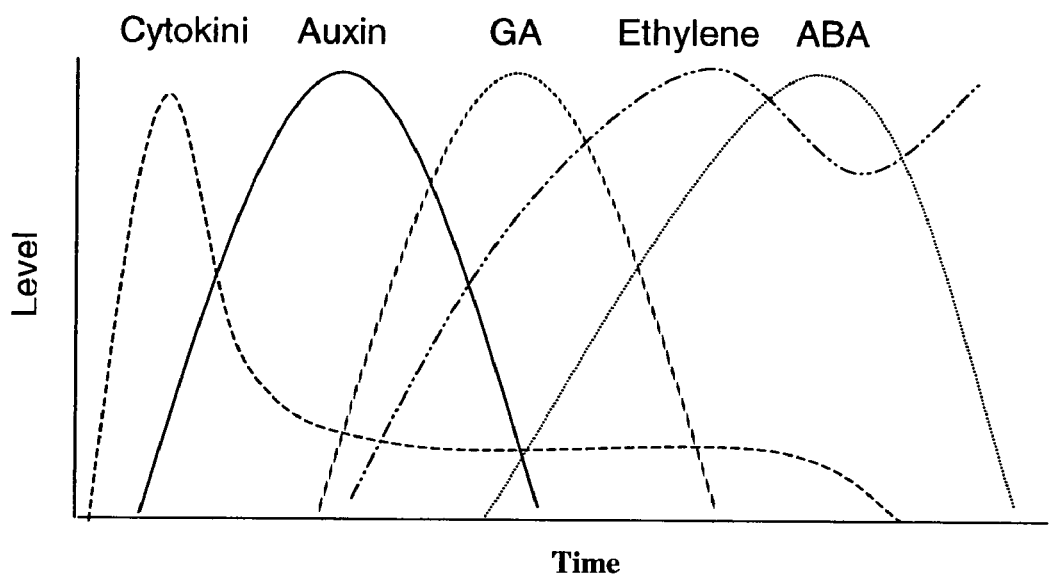
FIG. 1 is a graph illustrating the level of various plant hormones present in plant tissue during the plant growth cycle.

The auxin produced in the new shoot tissues travels down the stem to the roots, where it stimulates cell division to generate lateral root growth. As auxin is transported out of shoot tissues, it stimulates the synthesis of gibberellic acid (GA). Therefore, after the stage of cell division, gibberellin levels begin to rise in the tissue while cytokinin and auxin levels fall (Marschner 1986). If auxin transport does not occur, gibberellic acid biosynthesis will not occur (Wolbang and Ross, 2001). While auxin seems to be most responsible for the expansion of leaf cells, gibberellic acid plays an important part in the elongation of stem cells (Fosket 1994). A high level of auxin transport downward will generate greater biosynthesis of gibberellic acid, and thus longer internode length. Gibberellic acid also causes elongation of stolons in potato, and high gibberellic acid levels in potato stolons will prevent tuberization. During this period in which gibberellin dominates, cell size increases. See FIG. 1.

Toward the end of cell sizing, ethylene and abscisic acid (ABA) levels rise and cell maturity is reached. The auxin that was synthesized during the cell division stage stimulates not only gibberellic acid production, but also ethylene biosynthesis. Ethylene in turn stimulates ABA biosynthesis (Hansen and Grossman 2000). Ethylene and abscisic acid levels are responsible for tissue maturation and will eventually trigger senescence and death, once auxin, gibberellin and cytokinin levels decrease (Pessarakli 1994).

In addition to normal production during development, ethylene and abscisic acid can also be synthesized in response to plant stress. Often times a surge of reactive oxygen species coincides with increased ethylene (Abeles, et al., 1992). Abscisic acid and ethylene mediate several events associated with senescence and fruit ripening. Abscisic acid causes stomatal closure resulting in decreased carbon dioxide exchange and decreased photosynthesis, and abscisic acid inhibits sucrose mobilization by preventing phloem loading (Davies 1995). In addition several other events follow the increase in ethylene and abscisic acid during senescence and ripening including chloroplast breakdown, increased respiration, and protein and DNA degradation (Abeles et al 1992).

Sites of Hormone Synthesis and Distribution

Cytokinin is produced in meristematic tissues, primarily in the root, and can be transported to other tissues through the xylem and phloem (Pessarakli, 1994). Auxin is also produced in meristematic tissues, especially in shoots. Auxins can be transported downward through parenchyma cells via the action of polar auxin transporters, or can be transported in any direction through sieve tubes of the phloem (Pessarakli, 1994). Gibberellins are produced in growing tissues, with the highest concentrations of gibberellic acid being in roots and developing seeds, and lower concentrations in shoots and leaves. Gibberellic acid can be transported through both the xylem and the phloem. Abscisic acid is produced in all tissues and is transported to growing regions through either xylem or phloem. Ethylene is synthesized in all tissues and moves rapidly by diffusion (Pessarakli, 1994).

Plant Hormone Interactions

The growth of the plant is clearly a complex of responses to the interactions of many hormones. As stated earlier, it is well documented that a high cytokinin to auxin ratio will favor shoot development while a low cytokinin to auxin ration will favor root development (Pessarakli, 1994). These hormones also regulate the levels and possibly the transport of one another. Indole-3-acetic acid (IAA) can alter cytokinin levels and vice versa (Zhang et al 1996). In addition, other hormones affect the synthesis, degradation, and transport of one another. Gibberellic acid stimulates IAA oxidase activity to bring down IAA levels following the cell division stage. It is known that gibberellic acid can stimulate it's own biosynthesis through the repression of negative regulators of transcription (Gazzarrini and McCourt, 2003), and that IAA is required for gibberellic acid biosynthesis (Wolbang and Ross 2001). IAA has also been shown to stimulate the production of ethylene, and ethylene causes an increase in abscisic acid synthesis (Hansen and Grossman 2000).

In addition to regulating the levels of one another, the hormones also interact to affect plant processes as determined by the ratio of one hormone to another. High levels of abscisic acid and ethylene in young leaves will not induce senescence, and in young leaves auxin, gibberellic acid, and cytokinin levels are still relatively high. However in mature leaves, where auxin, gibberellic acid, and cytokinin levels have dropped, abscisic acid and ethylene do promote senescence. Thus, by changing the timing of the hormone fluxes in tissues, it is possible to change the timing of developmental events such as senescence.

Hormones also affect the transport of metabolites in the plant. Sucrose and gibberellic acid move in the opposite direction of IAA. In other words, in tissues where IAA levels are being reduced, either due to transport or degradation, gibberellic acid levels and subsequently sucrose levels rise. The mechanisms by which this process is mediated are unknown, but the transport of auxin conjugates appears to be involved in phloem loading (Davies 1995).

It is also interesting to note that many of the mineral nutrients associated in plant deficiencies are minerals involved in auxin metabolism. For example, zinc is a cofactor in auxin biosynthesis, and boron inhibits the IAA-oxidizing enzyme, thereby extending the half-life of IAA. Calcium is involved in auxin transport and auxin signaling pathways, and manganese and magnesium are cofactors for enzymes that liberate auxin from conjugate storage forms. Again, altering the nutrients that affect auxin content can skew the hormone balance and change the development of the plant.

While these interactions are complex and there are intensive areas of research on subsets of these interactions, we note one unifying factor. Relative levels of auxin and cytokinin to the other hormones seem to be central in the interaction of these hormone signals. While the mechanisms of plant hormone signaling pathways are unknown, the fact remains that an alteration of auxin or cytokinin levels will potentially alter these hormone interactions.

Photosynthate Movement

Photosynthates in a plant normally move in an opposite direction to the IAA gradient. When a plant is growing in a normal condition, IAA is produced in the apical meristem tissue and moves, by gravity, toward the basal part of the plant. When doing so, it directs the movement of photosynthates from mature leaves toward the apical meristem tissue of the plant. The rapid growth of a plant is merely an indication of the quantity of photosynthates that are moving from mature leaves to the apical meristem tissue of the plant. This would also indicate that the gradient of IAA movement downward increases as the rapidity of growth of the plant increases.

In most crops, movement of photosynthates toward the basal part of a plant are even more desirable than the movement of photosynthates to the apical meristem tissue. Some examples of this are potatoes, beets, onions and other crops with storage tissue that develop on the lower end of the plant. Perhaps, more importantly, the needs of roots for photosynthates are critical for the survival of a plant. As a plant tends to grow more rapidly, the root mass of a plant tends to decelerate in growth. This is primarily due to the lack of movement of photosynthates to the apical meristem tissue. This is particularly true for rapidly growing plants such as corn, bananas, cotton, soybeans and many other plants that make rapid vertical growth.

If one could decrease the gradient of IAA movement from the apical meristem tissue to the roots, then the sink of the roots and/or developing fruit on a plant would have a much greater capability of competing for photosynthates with the apical meristem tissue. In other words, if the gradient of IAA movement from the apical meristem tissue downward could be reduced, there would be greater root growth and fruit growth accompanied by uninterrupted supply of photosynthates to those tissues.

The reduction of IAA gradient and the consequent increase of root and fruit mass can be obtained by either the application of IAA and/or IBA in a constant supply to the roots so that the gradient of these two auxins moving upward in a plant is greater than the gradient of the natural occurring IAA produced at the apical meristem tissue to move down in the plant. This has been demonstrated through research trials on onions, peppers, corn and soybeans. Applications of these hormones are normally made on a weekly or bi-weekly schedule. This does not mean to imply that a greater frequency would not be preferable.

Another way to decrease the IAA gradient is a topical application of IAA and/or IBA to the upper portions of the plant. This would tend to equalize to the level of IAA and/or IBA in all of the above ground plant tissue. When obtaining a high level of IAA and/or IBA in the above plant tissue, the gradient of IAA is neutralized. This can be more effectively done with short intervals, e.g., two to three days, between these topical applications. Alternatively, these two auxins can be added, together with a boron solution, to maintain the activity of the IAA and/or IBA over a longer period of time. This is probably the preferred method of using IAA and/or IBA in regulating IAA gradient movement, because it eliminates more frequent applications and the costs associated therewith.

Tests involving the consistent application of IAA and/or IBA to corn plants through a drip irrigation system were conducted at Texas A&M University. Also, tests involving the topical application of IAA and/or IBA were conducted on corn trials at Texas A&M University. Both of these trials produced significantly increased corn yields. It was noted that the root mass and the stalk diameter of the corn plants were much greater where these two methods of application of IAA and/or IBA were applied to the corn plant.

One must realize that a corn stalk is merely made up of the basal portion of the corn plant leaves. Increasing the stalk diameter is an indication that more photosynthates are moving from the leaves down to the basil portion of the leaves. This would be reflected by an increase in the diameter of the stalk. This is exactly what is noted when the above two methods of applying IAA and/or IBA were tested with corn plants.

By being able to reverse the direction of photosynthate movement in a plant while it is growing, both larger roots and fruits should be produced. This is exactly what happened in the Texas A&M University experimental trials on onions, peppers and corn. The control of photosynthate movement within the plant by the administration of IAA and/or IBA is a revolutionary concept and application for counteracting the hormonal activity which is normally due to light sensitivity and the effects of gravity on a growing plant.

Hormonal Changes in Plants

Every plant tends to follow the same characteristic hormonal shifts as it goes through various stages of growth. When a seed is planted the hormonal shift is from abscisic acid (ABA) which causes seed dormancy toward gibberellic acid and/or auxin. This is an enzyme related activity, which causes the germination of the seed under proper moisture and temperature conditions. The first tissue that usually appears from the seed is the root.

Roots have the ability to synthesize cytokinin. Their ability to synthesize auxins is rather low. Therefore, in order to have adequate cell division the roots must receive a supply of IAA from the apical meristem tissue of new growth. It is a demand from the roots for additional IAA that forces the growing point and new leaves from a plant. New cell growth provides IAA to be transported downward to apical tissue of the root in order to trigger cell initiation and cell division. If the demand for IAA by the root system is greater then the upper portion of the plant can furnish, the root will trigger bud formation of new plants, which originate from the crown or the basal portion of the plant. This is manifested by suckering on corn, daughter plants on bananas, tillers on wheat, and vegetative stolons on potatoes.

As a plant undergoes its rapid growth stage, the bottom portion of the plant is shaded. This effect of light differential causes a more rapid movement of IAA in the apical meristem tissue of a plant downward toward the basal portion of a plant. This, in turn, initiates movement of gibberellic acid upward to the apical meristem tissue of the plant, resulting in increased internode length.

When the downward movement of IAA gradient increases, many vegetative and reproductive buds remain in dormancy. Dormancy of these buds will not be released until the gradient of the downward IAA movement in the plant is reduced. Therefore, when a plant is growing rapidly many of the buds of the main sterns are inactive. It has often been observed that a rapidly growing plant tends to have reduced flowering and vegetative bud initiation.

When the plant begins its reproductive cycle, i.e., flowering, the ratio of auxin to cytokinin is rapidly changed. During this period, the demand by the buds for auxin in order to accomplish cell division is high. The gradient of downward auxin movement in the plant can be significantly reduced, producing a curvature of the roots downward. This will also decrease the downward IAA gradient so that fruits are more capable of competing for photosynthates from mature leaves. This is important in order to provide a constant supply of photosynthates to the developing fruits. If this is not accomplished, many physiological disorders occur in the fruits during the period of development. During this period of fruit development, the fruit is constantly competing as a sink for photosynthates with the apical meristem growing tissue. It is important during this period that the competition of the apical meristem tissue for photosynthate sink is reduced compared to the sink of the fruit.

It is well known that multiple fruiting on a plant part such as a tomato truss or soybean raceme constantly compete for photosynthate supply. This is also common when noticing the fruit sizing on any cucurbit. The larger fruit is the more dominant fruit. It sizes at the expense of the fruit that are put in positions further away from the crown or the stem of the plant. This sequential sizing is caused by IAA dominance of the larger fruit over the small ones. This sequential sizing can be reduced through the application of an IAA and/or IBA material directly to the fruiting areas. This will enable the later sizing fruit to compete more favorably with those that size earlier. The reduction of sequential sizing is very important in trying to obtain uniformity of fruit, tubers and other reproductive plant parts.

During the period of ripening the combination of ethylene and ABA tend to dominate the plant cell, resulting in cell senescence. This senescence of plant cells in individual plant parts is normally referred to as ripening.

As can be seen from the above comments, different ratios of hormones are needed at different stages of growth. It is almost impossible to know exactly the ratio of various hormones in different plant species at different periods of growth. It is, therefore, proposed that auxin, cytokinin and/or gibberellic acid be applied in abundance at regular intervals to enable the plant to balance its own hormonal needs. This is critical to the use of plant growth hormones in order to control and increase the yield of crops. This is particularly important in obtaining the maximum genetic expression from any of the plant cells that are developing during any period of the plant's growth cycle.

In order to inhibit the effects of light (particularly red wavelength) it is necessary to control the movement of gibberellic acid inside the plant. This can be done by either using a gibberellic acid inhibitor or maintaining the stability of IAA in the apical meristem tissue, which in effect, regulates the activity of gibberellic acid that moves to the apical meristem tissue. The latter can be done by administering auxin (particularly IAA or IBA) to the upper part of the plant in such quantities or with another compound, which will maintain auxin concentration over a longer period of time. When doing so, the dominance of gibberellic acid in the plant cell is greatly retarded by the abundance of IAA in the apical meristem tissue.

The use of IAA as a topical application or applied through the root system with regular abundance can control the activity of gibberellic acid and thereby control the growth of the plant during periods of plant shading due to high plant population, or in case of a tree, the shading of the internal parts of the plant by the leaves of the tree.

The Function of Hormones in Tissues

The function of the root is to provide the nutrients, minerals, and water needed by the plant to survive and reproduce. The Stoller model also assumes that the root is the primary sensing organ of the plant, with the root cap functioning as a "thinking cap" to gather information about the outside conditions and communicate these conditions to other parts of the plant to initiate a response within the plant. There is a great deal of evidence for this theory. Numerous studies on gravitropic and touch responses have implicated the root cap in determining the direction in which the root should grow (Massa and Gilroy 2003, Boonsirichai, et al. 2002). Other studies, including some by Darwin, implicate the root cap in sensing other stimuli such as water potential (Eapen et al. 2003). The root cap is likely the region of the plant most responsible for sensing environmental conditions and altering the hormone balance of the plant accordingly. It has been shown that signals from the root cap can stimulate the formation of an auxin gradient in the root (Boonsirichai et al. 2002, Chen et al. 2002), and that this auxin gradient results in root bending to alter the direction of root growth. It is likely that root cap signals may be carried throughout the plant to alter the gradients of many hormones and affect growth according to the environment the root caps perceive. The Stoller model takes advantage of the role of the root cap in generating hormone signals through the application of plant hormones to the root area. Root application will be the preferred method of hormone application because it gives more consistent plant response due to the fact that the root cap is the growth control center as well as the natural source of many hormone signals.

Figure 2:
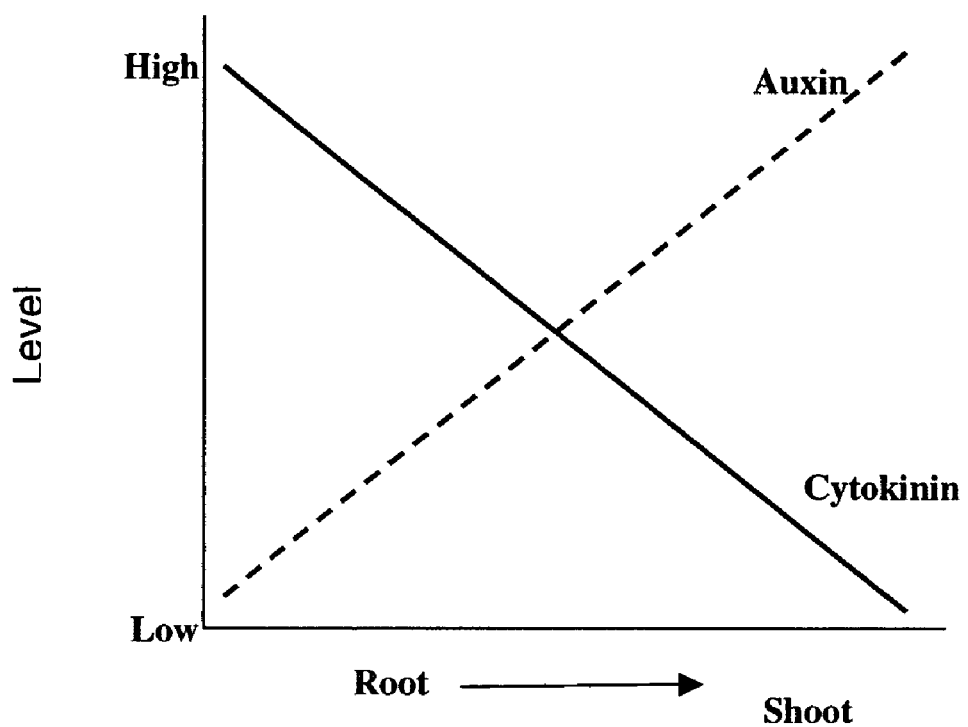
FIG. 2 is a graph illustrating the gradient of auxin to cytokinin in plant tissue between the roots and the shoots of the plant.

The function of the shoot is to provide energy for growth through photosynthesis, and to carry out reproductive processes. The shoot grows primarily in response to the conditions communicated from the root. The communications are likely perceived as a difference in the ratio of hormones to one another. The result of this communication is an alteration of growth. For example, if root growth has been prolific, the amount of cytokinin produced in new root tissues will be higher relative to levels when there is less growth. This cytokinin level will result in a change in the gradient of auxin to cytokinin that will increase the cytokinin content in aerial tissues and stimulate new cell growth. See FIG. 2. The greater the root mass, or the stronger the cytokinin production, the more shoot growth will be stimulated. Thus, a high amount of cytokinin in roots during the vegetative growth stage can sometimes lead to excessive growth of vines in potato, and can also stimulate the production of lateral branching in dicots. During this vegetative period, the addition of auxin to the root area will prevent this unwanted top growth.

IAA synthesized in new shoot tissues can then be transported to the root, or can be diverted to any tissue along the way. High IAA concentrations are also critical to bud development of flowers and fruit development. This is evidenced by the fact that when temperatures are very high during flower set and fruit set, there is a high rate of flower abscission and fruit malformation. This results because IAA synthesis is inhibited at higher temperatures (Rapparinini, et al 2002) possibly due to the temperature optima of the nitrilase genes involved in IAA biosynthesis (Vorwerk et al., 2001). When plants make the transition to flowering, new flower tissues generate a large supply of auxin. This auxin is then transported out of the flower. As fruit and seed develop, these tissues, too, synthesize high levels of IAA, which is transported out.

This auxin transport causes several things to happen. First, gibberellic acid biosynthesis is stimulated in these tissues as the auxin is transported. Second, the auxin stimulates the release of sugars from the leaves. High levels of IAA-ester conjugates in phloem have been correlated with increased phloem loading of sugars (Davies 1995). The sugar loaded into the phloem can then be transported into developing fruits, tubers, or other sink tissues.

Finally, and perhaps most importantly from a crop management standpoint, this auxin moves into root tissues. Although some auxin in root tissues is beneficial, oversupply is harmful. Because roots normally have very low levels of auxin, root tissue is very sensitive to auxin levels. In fact it takes 100-fold more IAA to cause shoot sensitivity than it does to cause root sensitivity (Davies 1995). As a result of the high sensitivity of roots to the auxin gradient, the transport of large quantities of IAA from fruiting bodies overloads these cells and inhibits root cell growth. This is evidenced by the observations that root decline coincides with fruit set in soybean, and soybean plants with higher pod numbers show faster decline. An overabundance of auxin can both inhibit cell division directly and increase the synthesis of ethylene and subsequently abscisic acid. This will ultimately lead to root senescence and plant death.

The physical manifestations of this mass exodus of auxin into the roots can be observed in many crops. In corn the number of adventitious roots, known as brace roots, will increase. In addition there will be an obvious downward turn of root growth and a decrease in meristematic root growth as evidenced by a lack of fine white roots. In legumes such as soybean and snap bean, this downward turn of the roots can also be observed, as can a decrease in meristematic roots and root nodules. In potatoes, loss of meristematic root growth occurs, and other stress symptoms appear such as vine decline and sometimes verticillium wilt. This early root death can be altered by inhibition of this auxin flux into the roots, either by altering the IAA side of the gradient, or by adding cytokinin to counteract the increase. Prolonging root life will prolong the period in which fruiting bodies fill and mature.

It is also important to note that these same conditions, i.e., an increase in auxin, abscisic acid, and ethylene, arise in roots when plants are under stress such as flooding, drought, and high salinity. Cytokinin application can reduce these stress hormone levels (Younis et al., 2003) and should therefore relieve the stress. The understanding that auxin production and transport actually becomes inhibitory to root growth is profound. Although it has been documented that auxin can be applied to roots at levels high enough to arrest root growth, it has never been suggested that the plant synthesizes enough auxin to bring about its own death. It has also been observed that the supply of cytokinin can delay or even abolish senescence, but it has never been suggested that this is due to a balancing of auxin that would otherwise lead to the production of factors that promote senescence in roots. In our ongoing experiments we are learning that cytokinin, when applied at or just before first flower, cannot only delay root decline, but can in fact increase meristematic roots to levels even higher than before flowering. This application will increase plant life and reduce plant stress, and has even been observed to alleviate symptoms of verticillium wilt infection in potato.

Because conditions for plant growth are never ideal as defined here, hormone levels are not always at optimum concentrations. By understanding how hormone levels change in response to the environment and development of the plant, we can learn how we can assist the plant to produce the results best for our particular situation. For example, if temperatures have been very high or very low, we understand that the plant will be unable to produce auxin, and we can supplement it. Likewise we can alter the auxin and cytokinin gradients at different times of development to alter growth toward that which is most beneficial for that particular crop situation. When plants are very young, in the seedling or new transplant stage, auxin should be applied to the roots. This will stimulate early root establishment and will be evident in plants that take hold faster and initially produce true leaves earlier than untreated plants. Low levels of auxin supplied to the roots throughout the vegetative stage will be beneficial in establishing and maintaining healthy roots, and will keep vineing down in sweet potato and irish potato.

Most growers skilled in the art know the appropriate internode length for their crop. If a grower wants to reduce the internode length of new shoot growth, an application of auxin to the roots will accomplish this. If internode length should be increased, an application of gibberellic acid to the shoots will deliver results. Likewise experienced growers know the appropriate amount of top growth for their crop. If top growth is too prolific, addition of auxin to the roots will slow new shoot development. If more top growth is desired, addition of cytokinin to the roots will stimulate more shoot growth and more branching. If a grower notices excessive flower abortion, a spray of auxin will help with retention. After plants have made the transition to flower, they oversupply auxin to the roots. Therefore cytokinin should be applied to the roots to balance this high level of auxin being transported down from flowers and fruits. In addition, if plants are under stress from heavy fruit load, flooding, drought, saline soils, or pathogen infection, ethylene and abscisic acid build up in the roots. Cytokinin should again be applied to correct this problem. Addition of cytokinin to the root area will balance the effects of excess auxin, abscisic acid, or ethylene and prolong root life.

Through these applications it is possible to increase root size, extend root life, decrease internode length, increase lateral branching, regulate the appearance of new top growth and increase fruit quality. Through the methods of this invention, growers will gain an understanding of how crops grow and how to assist the crop plants to produce the maximum yield from their potential.

The present invention is directed to methods for controlling the growth of plant tissues by manipulating the levels and ratios of plant hormones in the plant tissue, particularly in the roots of the plants. By manipulating there hormone levels and ratios, growth of the plant can be controlled to increase root size, extend root life, alter internode length, increase lateral branching, regulate appearance of new top growth and increase fruit quality.

In the methods of the present invention, a plant hormone, e.g., an auxin, in an amount effective to produce the desired improved plant architecture and the resulting improvement in plant growth and productivity is applied to the plant tissue. While the auxin is applied in an amount sufficient to produce the desired result, it must be applied in an amount insufficient to negatively affect growth of plant tissue. Alternatively, the level, ratio or effectiveness of endogenous or applied hormone may be manipulated to fall within ranges to produce those results. The desired manipulation can be achieved by applying other plant growth regulators (PGRs), e.g., plant hormones such as the kinetins and gibberellins, more specifically cytokinin and gibberellic acid, and their precursors and/or derivatives in effective amounts.

The presently preferred plant hormones for use in the methods of the present invention are the auxins. Auxins useful in the methods of the present invention are selected from the group consisting of the natural auxins, synthetic auxins, auxin metabolites, auxin pre-cursors, auxin derivatives and mixtures thereof. The preferred auxin is indole-3-acetic acid (IAA), a natural auxin. The preferred synthetic auxin is indole-3-butyric acid (IBA). Other exemplary synthetic auxins which may be employed in the methods of the present invention include indole propionic acid, indole-3-butyric acid, phenylacetic acid, naphthalene acetic acid (NAA), 2,4-dichlorophenoxy acetic acid, 4-chloroindole-3-acetic acid, 2,4,5-trichlorophenoxy acetic acid, 2-methyl-4-chlorophenoxy acetic acid, 2,3,6-trichlorobenzoic acid, 2,4,6-trichlorobenzoic acid, 4-amino-3,4,5-trichloropicolinic acid and mixtures thereof. Other plant growth hormones which act by altering the level or effectiveness of endogenous or applied auxin within the plant tissue may also be applied. These hormones (PGRs) may include ethylene, cytokinins, gibberellins, abscisic acid, brassinosteroids, jasmonates, salicylic acids and precursors and derivatives thereof.

In one embodiment of the methods of the present invention, the plant hormone, e.g., an auxin or another PGR, is applied to the seeds or tubers of the plant prior to planting. When applied to the seeds or tubers, e.g., to bean seeds or potato pieces, respectively, an auxin should be applied at a rate of about 0.0028 to about 0.028 grams auxin per 100 kg seed weight. In a more preferred embodiment, the auxin is applied to seeds, e.g., bean seeds, at a rate of about 0.016 to about 0.112 grams auxin per 100 kg seed weight. On the other hand, when applied to potato seed pieces, the auxins should be applied at a rate to result in about 0.125 to about 2.8 grams auxin per hectare of planted seed pieces. In a more preferred embodiment, the rate of application to potato seed pieces should result in about 0.125 to about 0.28 grams auxin per hectare of planted seed pieces. When applied to the roots, foliage, flowers or fruits of plants, the auxin should be applied at a rate of about 0.0002 to about 0.06 grams auxin per hectare per day, more preferably at a rate of about 0.002 to about 0.01 grams auxin per hectare per day. Application may be made over a series of days during the growing period based upon perceived stress on the plants and observed infestation. Alternatively, another PGR may be applied at a rate sufficient to manipulate the level of endogenous and/or applied auxin to within the stated ranges.

In a more preferred embodiment of the methods of the present invention, the hormone is applied to the roots, foliage, flowers or fruits of a plant after planting. While application to the roots or tubers prior to planting or by soil application after planting, may produce the best results in some circumstances, in others, application to the foliage may be preferred. The specific crop and the desired result must be taken into account when selecting an application method.

The plant hormone, e.g., an auxin or another PGR, may be applied as an aqueous solution or as a powder. When applied as an aqueous solution, the solution may include a metal selected from the group consisting of the alkaline earth metals, the transition metals, boron and mixtures thereof. Preferred metals include calcium, magnesium, zinc, copper, manganese, boron, iron, cobalt, molybdenum and mixtures thereof. Most preferred are calcium and boron. When included, the metal may be present in a range from about 0.001 to about 10.0 percent-by-weight, preferably from about 0.001 to about 5.0 percent-by-weight. The preferred method of applying the PGRs may be along with a boron-containing solution, including up to about 10.0 percent-by-weight boron.

Boron will tend to stabilize the auxins in plant tissues to which such solutions are applied.

The application of a metal, preferably boron, together with the PGR appears to extend the effective life of the PGR, thus permitting longer times between repeat applications. Boron appears to improve the efficacy, both the life and activity, of added IAA by suppressing the activity and or synthesis of IAA-oxidase, the enzyme that degrades IAA in plants. The anti-oxidant ascorbic acid may be part of the mechanism through which boron enhances IAA activity. Boron also enhances sugar transport in plants, cell wall synthesis, lignification, cell wall structure through its borate ester linkages, RNA metabolism, DNA synthesis, phenol metabolism, membrane functions and IAA metabolism. Further, boron is known to modulate respiration. The boron requirement for reproductive growth is higher than that for vegetative growth. Boron interacts with auxin especially in cell elongation such as pollen tubes, trichomes and other cells. Boron also stimulates auxin-sensitive plasmalemma NADH-oxidase and is necessary for the auxin stimulation of ferricyanide-induced proton release in plant cells. Boron is also part of the endocytosis mechanism of rhamnogalacturonan II dimers (linking through di-ester bonds) in formation of primary walls in dividing cells such as root tips, trichomes or pollen tubes. Thus, boron is linked with auxin-mediated cell division as well as auxin-mediated cell elongation. Finally, boron has been reported to have anti-fungal and anti-bacterial activities. Accordingly, it is believed that application of PGRs, together with boron, will improve the effect of the PGR in suppressing insect and pathogen infestation in plants.

The active half-life of IAA and IBA is rather short. This is due to the ability of the plant to metabolize these two auxins. IAA oxidase is the enzyme that is responsible for the catabolism of IAA. One of the functions of gibberellic acid is to increase IAA oxidase, so that gibberellic acid can control cell growth. On the other hand, boron decreases the level of IAA oxidase. One can readily see that an adequate amount of boron will extend the half-life of IAA and/or IBA by reducing IAA oxidase, the enzyme that degrades these two hormones.

If IAA and IBA are combined with a boron-containing material, it will allow the auxins to exert more influence over cell growth, cell division, and the dominance of the cell by gibberellic acid. This is clearly shown by the use of PGRs in conjunction with a boron solution containing methyethylamine (MEA). When applied as a topical application to crops, internode length was reduced and both stem diameter and root mass were increased. These growth characteristics clearly show that the dominant activity of gibberellic acid is reduced in the plant. This is similar to the way a plant grows at lower temperatures in the range of about 22° C.

When applied as an aqueous solution, a solution containing the plant hormone, e.g., an auxin or another PGR, may be sprayed on seeds or tubers using conventional spray equipment. Alternatively, the seeds or tubers may be immersed in an aqueous solution of the hormone.

When applied to the roots, foliage, flowers or fruits of plants, an aqueous solution containing the hormone, e.g., an auxin or another PGR, may be applied using conventional irrigation or spray equipment. Alternatively, the hormone may be applied in a dry form as a powder. When so applied, the hormone is mixed with a biologically and environmentally compatible material. Such a powder may be applied to the foliage, flowers or fruits by conventional dusting equipment.

Alternatively, the powder may be encapsulated in a biologically compatible material to provide for slow release when placed on or near the seeds, tubers or roots of the plant. Such encapsulated materials may be placed directly on the seeds or tubers or may be dispersed within the root zone of the plant where the slowly released auxin may be absorbed by the roots. Exemplary biologically compatible materials useful in encapsulation include the clays, lignites, resins, silicones and mixtures thereof.

While the methods of the present invention may be used with substantially all plants, they are particularly useful when applied to crop plants, e.g., dry beans, soy beans, onions, cucumbers, tomatoes, potatoes, corn, cotton and the like.

Finally, the present invention includes seeds and seed pieces for producing plants which have been treated in accord with the present invention. Such seed pieces include a plant seed or seed piece having dispersed on the surface thereof a plant hormone, e.g., an auxin or another PGR, in an amount effective to inhibit growth of harmful organisms in or on tissues of the plant, but in an amount insufficient to negatively affect growth of the plant tissues. Alternatively, such seeds and seed pieces have dispersed on the surface thereof a PGR in an amount sufficient to manipulate the endogenous and/or applied hormone level or ratio to within a range for producing the desired result. Such seed pieces may be prepared by spraying an aqueous solution of the hormone, e.g., an auxin or another PGR, onto the surface of seeds or seed pieces. Alternatively, the seeds or seed pieces may be immersed in an aqueous solution of the hormone. In the presently preferred embodiment, the hormone is present in an amount of about 0.0028 to about 0.028 grams of auxin per 100 kg seed weight of beans and similar seeds. Where the seed piece is a potato seed piece, the auxin, in the presently preferred embodiment, is present in an amount to result in about 0.0125 to about 2.8 grams auxin per hectare of planted seed pieces.

Following are several examples of use of the methods of the present invention to effect the growth of various plants. These examples are provided by way of illustration only and are not intended to limit the scope of the invention in any way.

EXAMPLE 1

Figure 3:
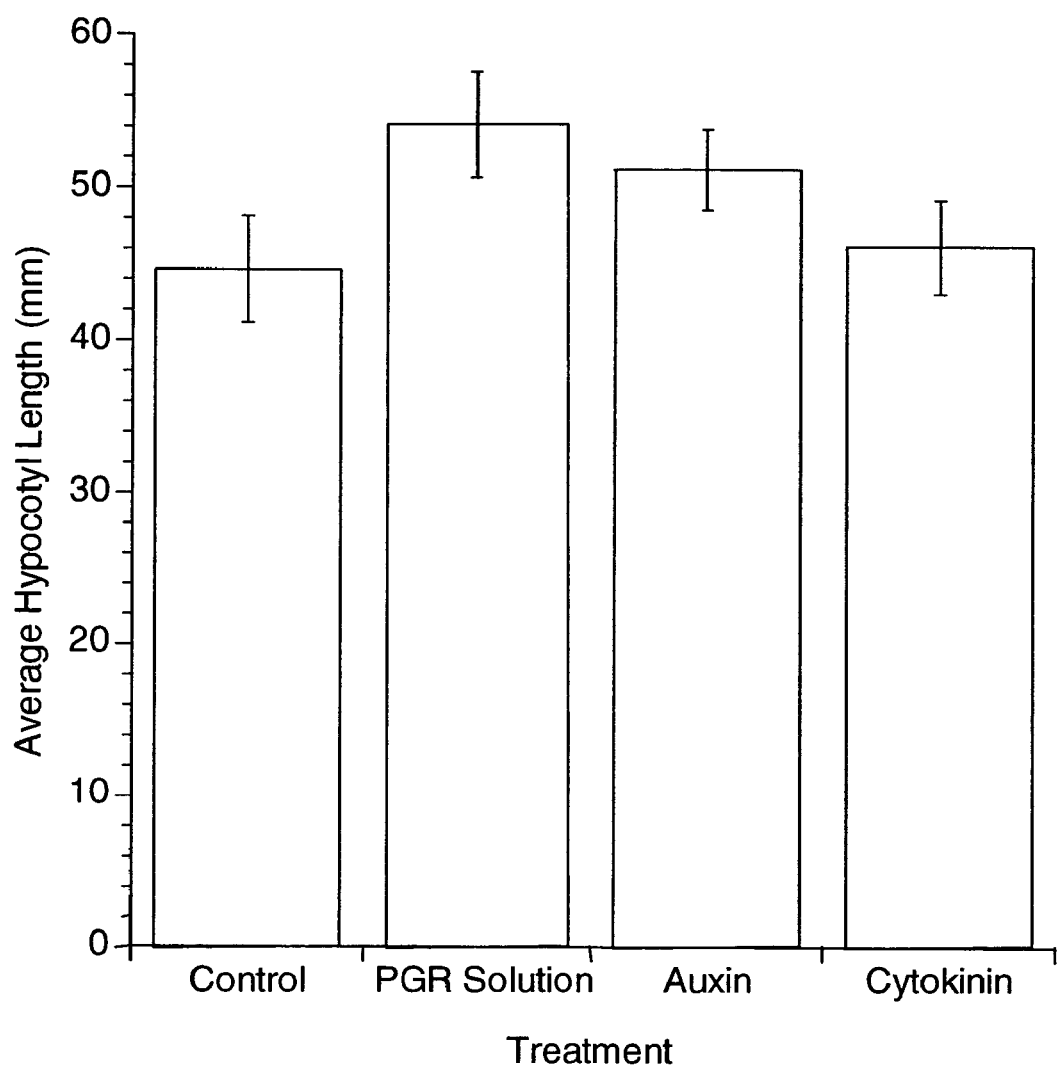
FIG. 3 is a bar graph illustrating the effect on hypocotyl length resulting from treatment of radish plants with various plant hormones in accord with the present invention as summarized in Table I.
Figure 4:
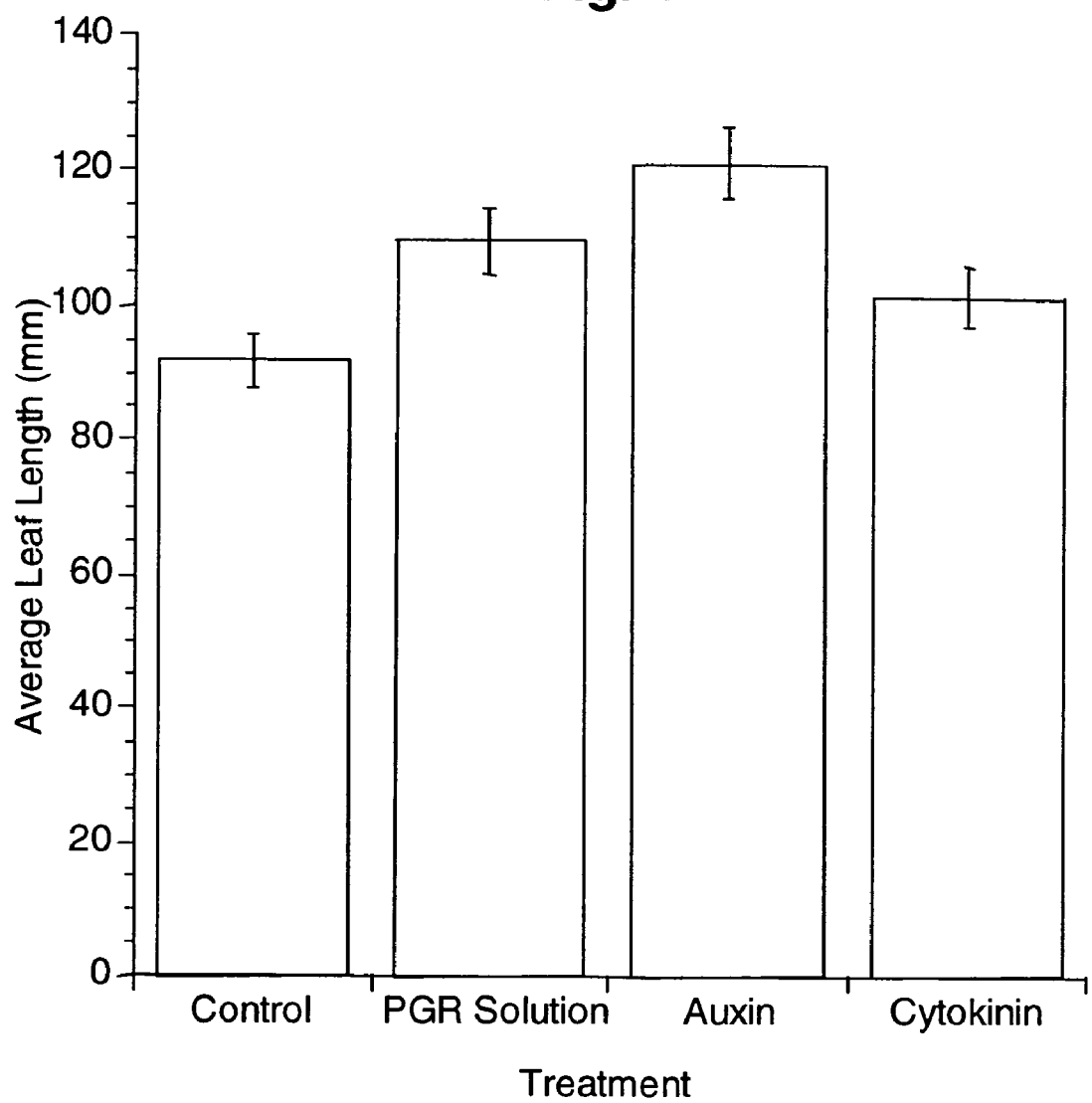
FIG. 4 is a bar graph illustrating the effect on leaf length resulting from treatment of radish plants with various plant hormones in accord with the present invention as summarized in Table I.

In this experiment, the effects of PGRs on radish growth were observed. A total of eighty (80) plants were used for this experiment. Twenty (20) plants were treated with water as a control. Twenty (20) plants were treated with a PGR solution corresponding to a rate of 12 oz/acre. The PGR solution is an aqueous solution including 0.015% IAA, 0.005% IBA, 0.009% cytokinin and 0.005% gibberellic acid as active ingredients. Also present as inactive ingredients are 1.000% emulsifier, 0.850% surfactant and 0.050% defoamer. A small measure, 0.0084 ml of this solution, was diluted into 100 ml of water and applied to the soil of a container having a surface area of about 1 square foot to correspond to an application rate of 12 oz/acre. Twenty (20) plants were treated with an auxin solution containing indole-3-acetic acid (IAA) at a rate of 0.84 micrograms in 100 ml water per square foot of surface area of the container. Finally, twenty (20) plants were treated with the cytokinin kinetin at a rate of 0.84 micrograms in 100 ml water per square foot of surface area of the container. Treatments were applied to soil at the time of planting and repeated every week thereafter. Length of the hypocotyl and largest leaf of each plant was measured 21 days after planting. The mean hypocotyl length and leaf length was calculated. Results are tabulated in Table I and illustrated in FIGS. 3 and 4.

TABLE I

Effects of PGR on Radish Growth

| Treatment | Average Hypocotyl Length (mm) | Average Leaf Length (mm) |
|---|---|---|
| Control | 44.70 ± 3.50 | 91.75 ± 3.99 |
| PGR solution | 54.10 ± 3.42 | 109.65 ± 4.87 |
| Auxin | 51.15 ± 2.64 | 121.15 ± 5.20 |
| Cytokinin | 46.10 ± 3.10 | 101.25 ± 4.46 |

Hypocotyl and leaf lengths are expressed in millimeters ± standard deviation of the mean.

Treatments in accord with the present invention, whether using a single hormone, e.g., an auxin or cytokinin, or a combination as provided by the PGR solution result in production of leaves characterized by both increased average leaf length and average hypocotyl length.

Figure 5:
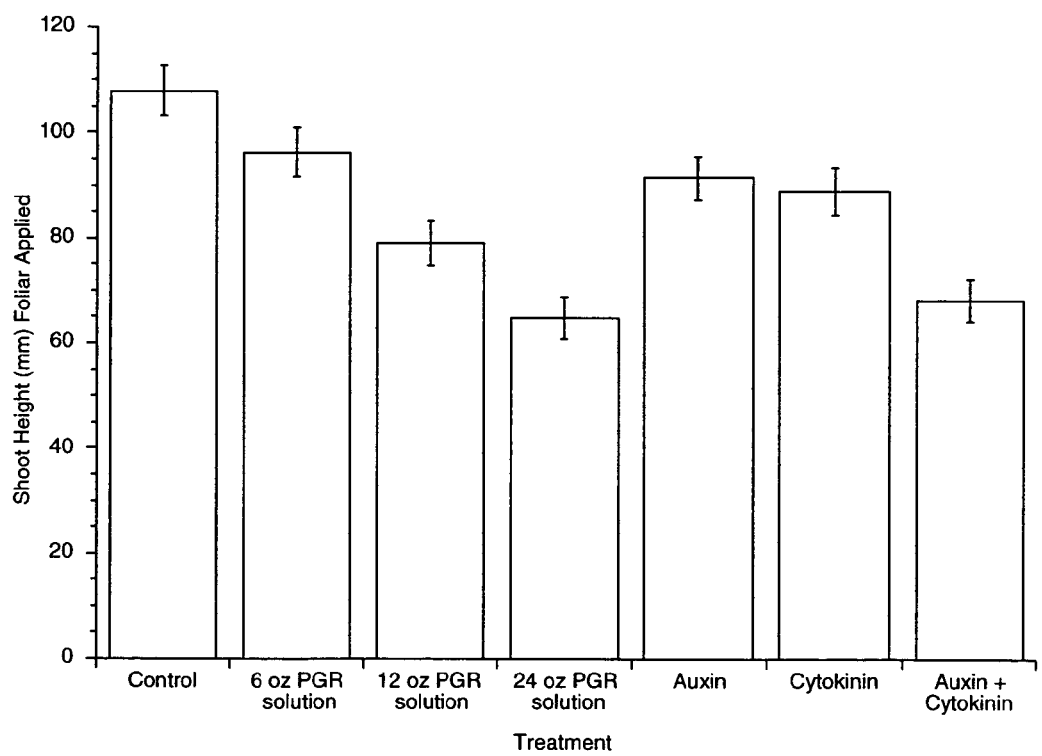
FIG. 5 is a bar graph illustrating the effect on average shoot height resulting from foliar applied treatment of radish plants with various plant hormones in accord with the present invention as summarized in Table II.

In this portion of the experiment radish plants were treated twice at four day intervals. Plants were treated first on emergence, and again four (4) days later. Measurements were taken one week after the last treatment. Treatments are equivalent to 6 oz/acre, 12 oz/acre, and 24 oz/acre of PGR solution, while the IAA and kinetin treatments are equivalent to the relative amounts in the 6 oz/acre rate of PGR solution. The second treatment was applied two inches to the left of the seedlings and, therefore, did not contact the seedling roots. The results of these experiments are tabulated in Table II and illustrated in FIG. 5.

TABLE II

Radish Height Data

| Treatment | Shoot Height (mm) Foliar Applied |
|---|---|
| Control | 107.89 ± 4.65 |
| 6 oz PGR solution | 96.23 ± 4.62 |
| 12 oz PGR solution | 79.04 ± 4.22 |
| 24 oz PGR solution | 64.77 ± 4.02 |
| Auxin | 91.46 ± 4.20 |
| Cytokinin | 89.00 ± 4.55 |
| Auxin + Cytokinin | 68.36 ± 3.97 |

Shoot height is expressed in millimeters ± standard deviation of the mean. Sample size is 15 plants.

EXAMPLE 2

Figure 6:
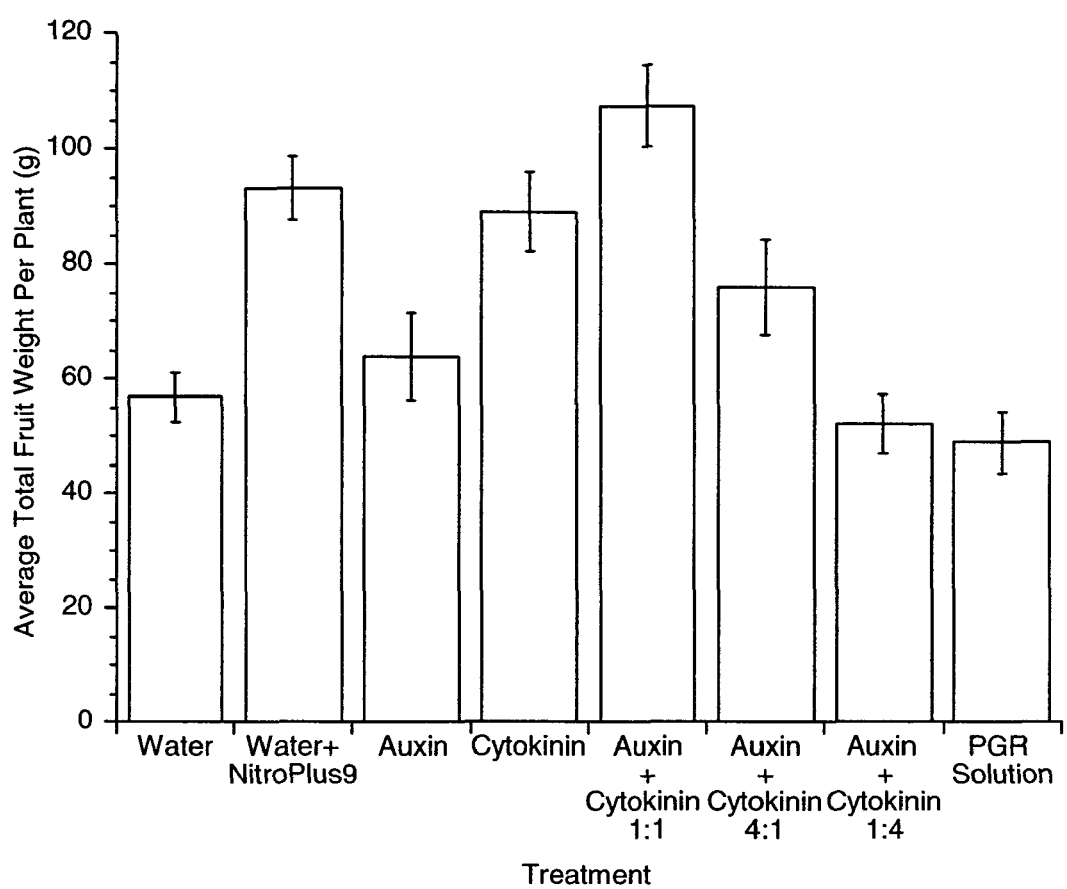
FIG. 6 is a bar graph illustrating the effect on the average total fruit weight of tomatoes produced from plants treated with various plant hormones in accord with the present invention as summarized in Table III.
Figure 7:
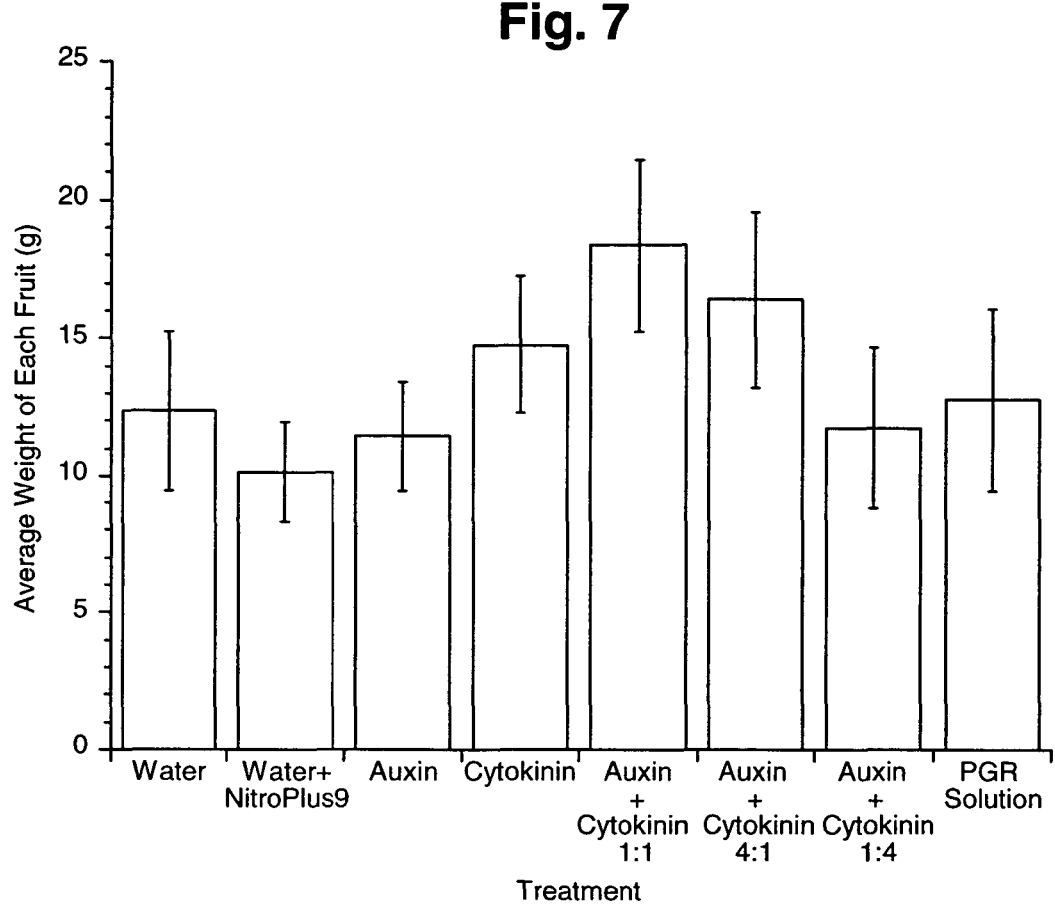
FIG. 7 is a bar graph illustrating the effect on the average fruit weight of individual tomatoes produced from plants treated with various plant hormones in accord with the present invention as summarized in Table III.

In this experiment, the effects of PGRs on tomato yield were determined. Tomato variety TSH04, which is a processing tomato, was used. All plants were grown in five gallon pots in a greenhouse. Eight plants were used for each treatment. Application of the treatments was done aerially to eight plants and in the soil for eight plants to allow comparison of soil versus foliar application of the PGRs. Treatments were 6 oz/acre PGR solution. The treating solutions were prepared by diluting 0.0042 ml of concentrated solution into 100 ml water for application to the soil, or into 50 ml water for foliar application. The IAA solution was prepared by diluting 0.42 micrograms of IAA into 100 ml water for application to the soil, or into 50 ml water for foliar application. The cytokinin solution was prepared by diluting 0.42 micrograms of kinetin into 100 ml water for application to the soil, or into 50 ml water for spraying of the foliage. The solution containing both IAA and kinetin at a 1:1 ratio was prepared by diluting 0.42 micrograms of IAA and 0.42 micrograms of kinetin into 100 ml water for application to the soil, or into 50 ml water for foliar application. A solution containing both IAA and kinetin at a 4:1 ratio was prepared by diluting 0.42 micrograms of IAA and 0.11 micrograms of kinetin into 100 ml water for soil application, or into 50 ml water for foliar application. Finally, a solution containing both IAA and kinetin at a 1:4 ratio was prepared by diluting 0.11 micrograms of IAA and 0.42 micrograms of kinetin into 100 ml water for soil application, or into 50 ml water for foliar application. Water was employed as a control. Plants were kept pruned to one fruiting truss per plant and the weight of the fruit from each plant was measured when most of the fruit had ripened (112 days after planting). Results are tabulated in Table III. FIGS. 6 and 7 illustrate the increased fruit weight achieved, respectively, for total and individual fruits with each treatment.

TABLE III

Effects of PGRs on Total Fruit Weight

| Treatment | Average total fruit weight per plant (grams) | Average weight of each fruit (grams) |
|---|---|---|
| Water | 56.79 ± 4.28 | 12.36 ± 2.90 |
| Water + NitroPlus9 | 93.19 ± 5.49 | 10.13 ± 1.84 |
| Auxin | 63.79 ± 7.59 | 11.45 ± 1.99 |
| Cytokinin | 89.08 ± 6.85 | 14.76 ± 2.47 |
| Auxin + Cytokinin 1:1 | 107.41 ± 6.99 | 18.34 ± 3.12 |
| Auxin + Cytokinin 4:1 | 75.90 ± 8.24 | 16.38 ± 3.16 |
| Auxin + Cytokinin 1:4 | 52.19 ± 5.23 | 11.73 ± 2.92 |
| PGR solution | 48.83 ± 5.49 | 12.75 ± 3.29 |

Fruit weight is expressed in grams ± standard deviation of the mean. NitroPlus9 is a solution containing, as active ingredients, amines complexed with calcium or magnesium chloride. NitroPlus9 is a trademark of Stoller Enterprises, Inc.

Tomato plants treated in accord with the present invention appear to generally produce more and heavier fruit, particularly where the treating solution includes both and auxin and cytokinin in equal parts.

EXAMPLE 3

Figure 8:
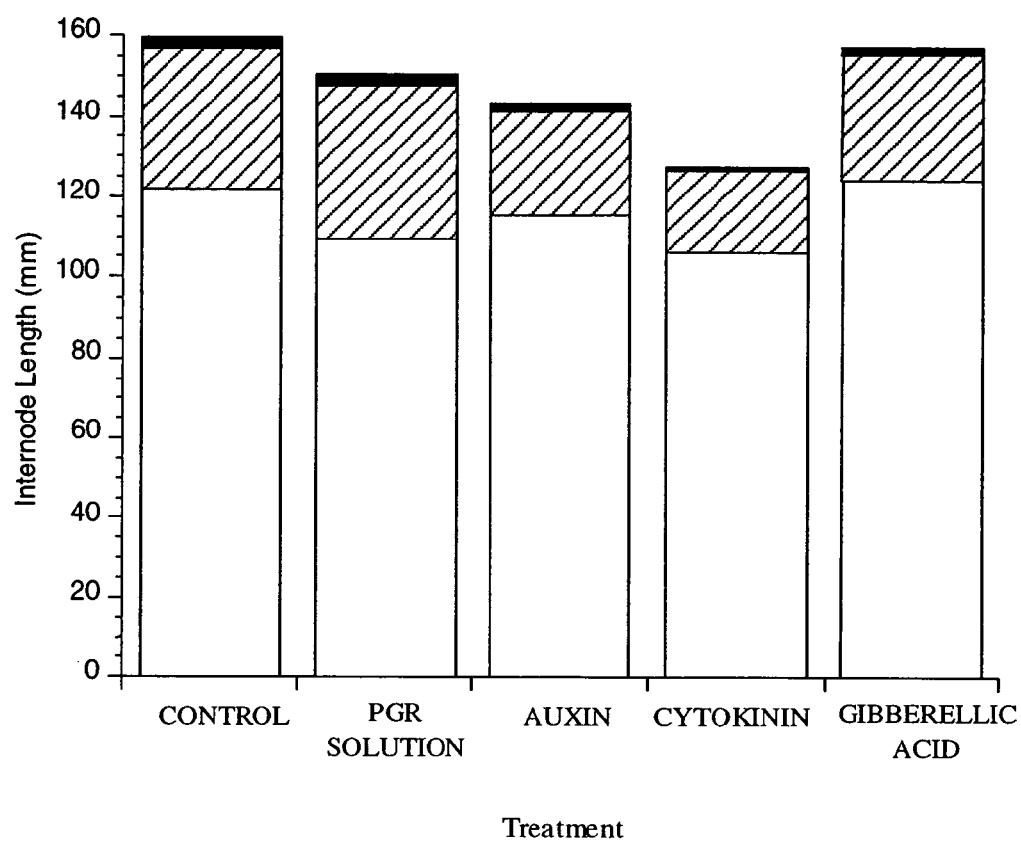
FIG. 8 is a bar graph illustrating the length of, respectively, the first, second and third internodes resulting from treating cucumber plants with different plant hormones, either alone or in combination, in accord with present invention as summarized in Table IV.

In this experiment, the effect of PGRs on cucumber internode length was determined. The cucumber variety used was the National pickling cucumber distributed by NK Lawn & Garden Co. (Chattanooga, Tenn.). Eight plants were used per treatment. Treatments were applied to the soil of each five-gallon pot containing one plant per pot. Treatments were 6 oz/acre PGR solution. The final PGR solution was prepared by diluting 0.0042 ml of the concentrated solution into 100 ml water. The IAA solution was prepared by diluting 0.42 micrograms of IAA into 100 ml water. The cytokinin solution was prepared by diluting 0.42 micrograms of kinetin into 100 ml water. Finally, plants were treated with 6 oz/acre N-Large. The treating solution was prepared by diluting 0.0042 ml of the commercial solution into 100 ml water. N-Large is a formulation containing 4 percent gibberellin (GA3). Water was used as a control. Treatments were applied to the soil at the time of planting, and weekly thereafter. Twenty-one (21) days after planting, the internode length of the first (bottom), second (middle), and third (top) internodes were measured to the nearest millimeter. The average internode length for first, second, and third internodes was calculated for each treatment. Results are tabulated in Table IV and illustrated in FIG. 8.

TABLE IV

Effects of PGRs on Cucumber Internode Length

| Treatment | Internode 1 | Internode 2 | Internode 3 |
|---|---|---|---|
| Control | 122.00 ± 4.13 | 35.00 ± 4.36 | 8.25 ± 2.50 |
| PGR solution | 109.63 ± 4.11 | 38.00 ± 4.21 | 9.25 ± 2.97 |
| Auxin | 115.88 ± 4.01 | 25.38 ± 3.13 | 4.50 ± 1.91 |
| Cytokinin | 106.38 ± 3.98 | 20.25 ± 3.40 | 2.13 ± 1.25 |
| Gibberellic Acid | 124.38 ± 3.80 | 31.00 ± 3.68 | 4.63 ± 2.13 |

Internode length is measured in millimeters ± standard deviation of the mean.

Cucumbers were harvested and weighted to the nearest gram eighty-four (84) days after planting. At the same time, the total vine length was measured to the nearest millimeter. In addition, the number of internodes and number of branches were also counted. Average vine length, average internode number, average branch number, average internode length and average cucumber weight were determined. Results are tabulated in Table V and illustrated in FIGS. 9a-9e.

TABLE V

Effects of PGRs on Cucumber Vines and Fruit

| Treatment | Average Vine Length (mm) | Average Internode Number | Average Branch Number | Average Internode Length (mm) | Average Cucumber Weight (gm) |
|---|---|---|---|---|---|
| Control | 301.0 ± 7.14 | 31.00 ± 2.38 | 2.6 ± 1.3 | 9.74 ± 0.57 | 294.91 ± 7.75 |
| PGR Solution | 289.75 ± 5.55 | 33.00 ± 1.57 | 4.75 ± 1.58 | 8.79 ± 0.88 | 352.06 ± 6.87 |
| Gibberellic Acid | 252.38 ± 4.56 | 27.63 ± 1.46 | 5.13 ± 1.55 | 9.14 ± 0.62 | 242.66 ± 9.67 |
| Kinetin | 255.50 ± 5.61 | 30.50 ± 1.75 | 6.25 ± 2.27 | 8.37 ± 0.62 | 229.71 ± 1.33 |
| IAA | 267.00 ± 5.70 | 30.75 ± 1.96 | 7.25 ± 1.86 | 8.72 ± 0.87 | 311.98 ± 9.17 |

Vine length and internode length were measured to the nearest millimeter.
Internode length was calculated by dividing the vine length by the internode number.
Cucumber weight was measured to the nearest gram.
All measurements are shown ± the standard deviation of the mean.

EXAMPLE 4

Figure 10A:
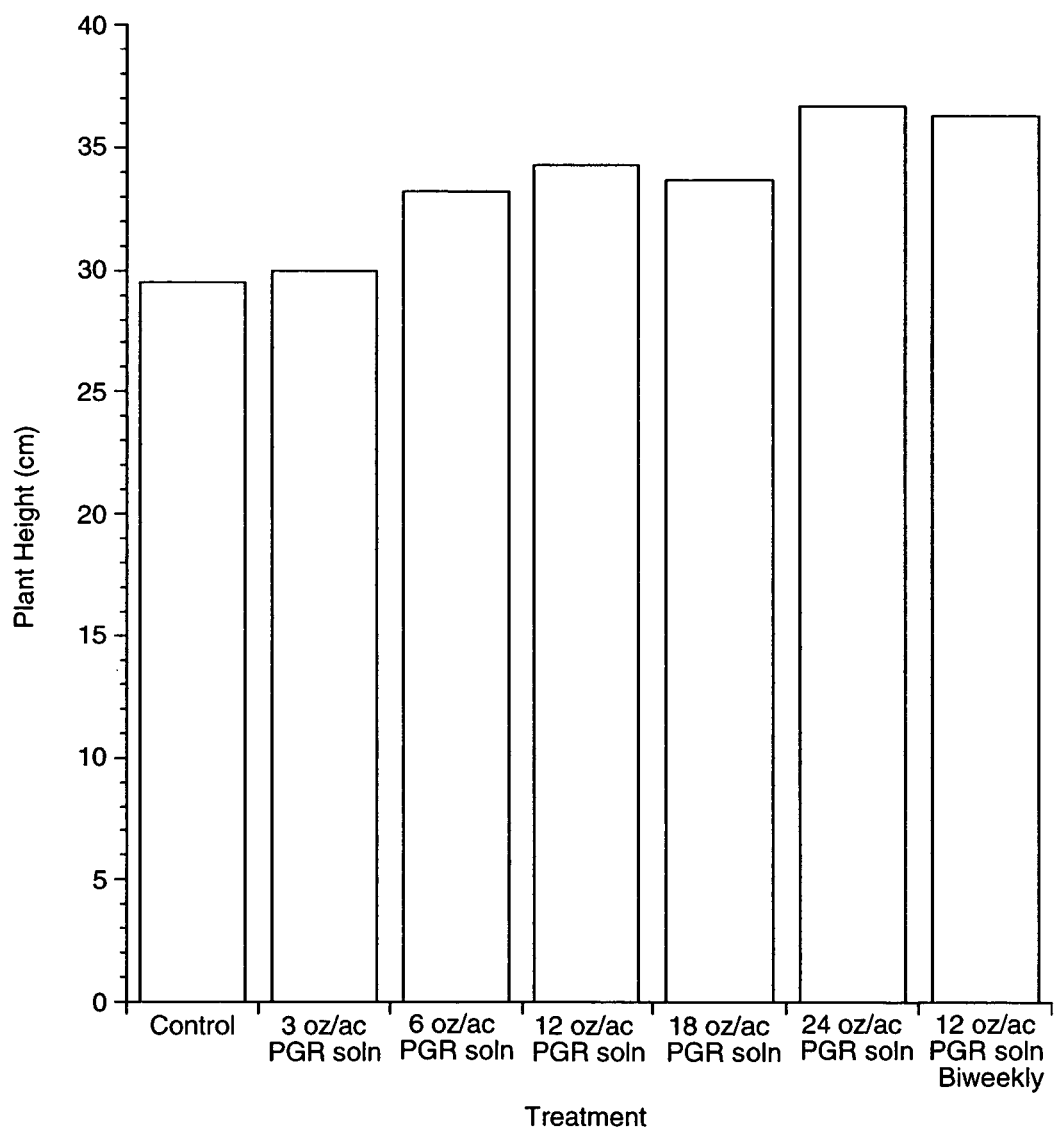
FIGS. 10a-10c are bar graphs illustrating, respectively, the average plant height, canopy diameter and root weight of pepper plants treated with various dosage rates of a plant growth regulator solution in accord with the present invention as summarized in Table VI.
Figure 10B:
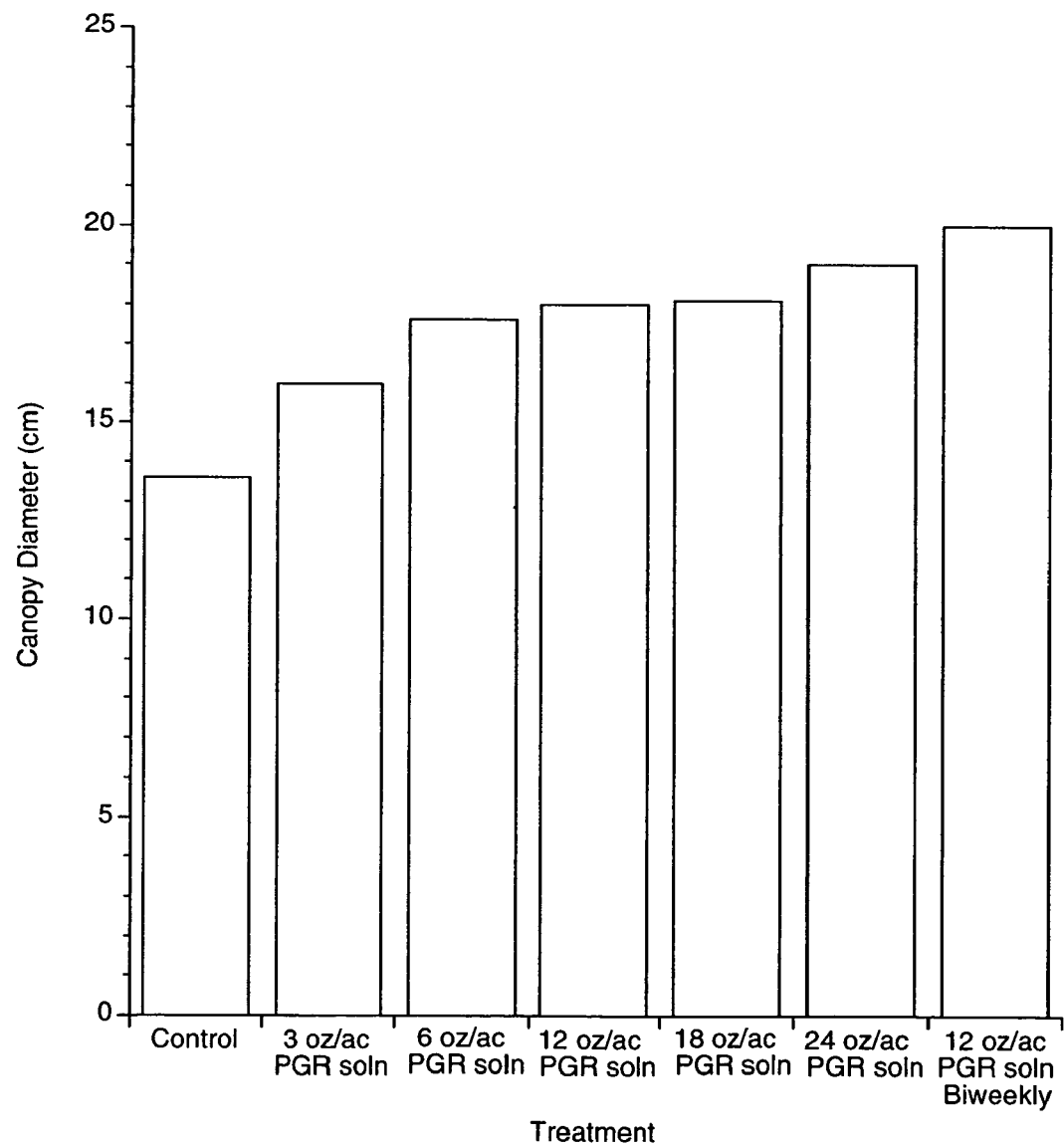
Figure 10C:
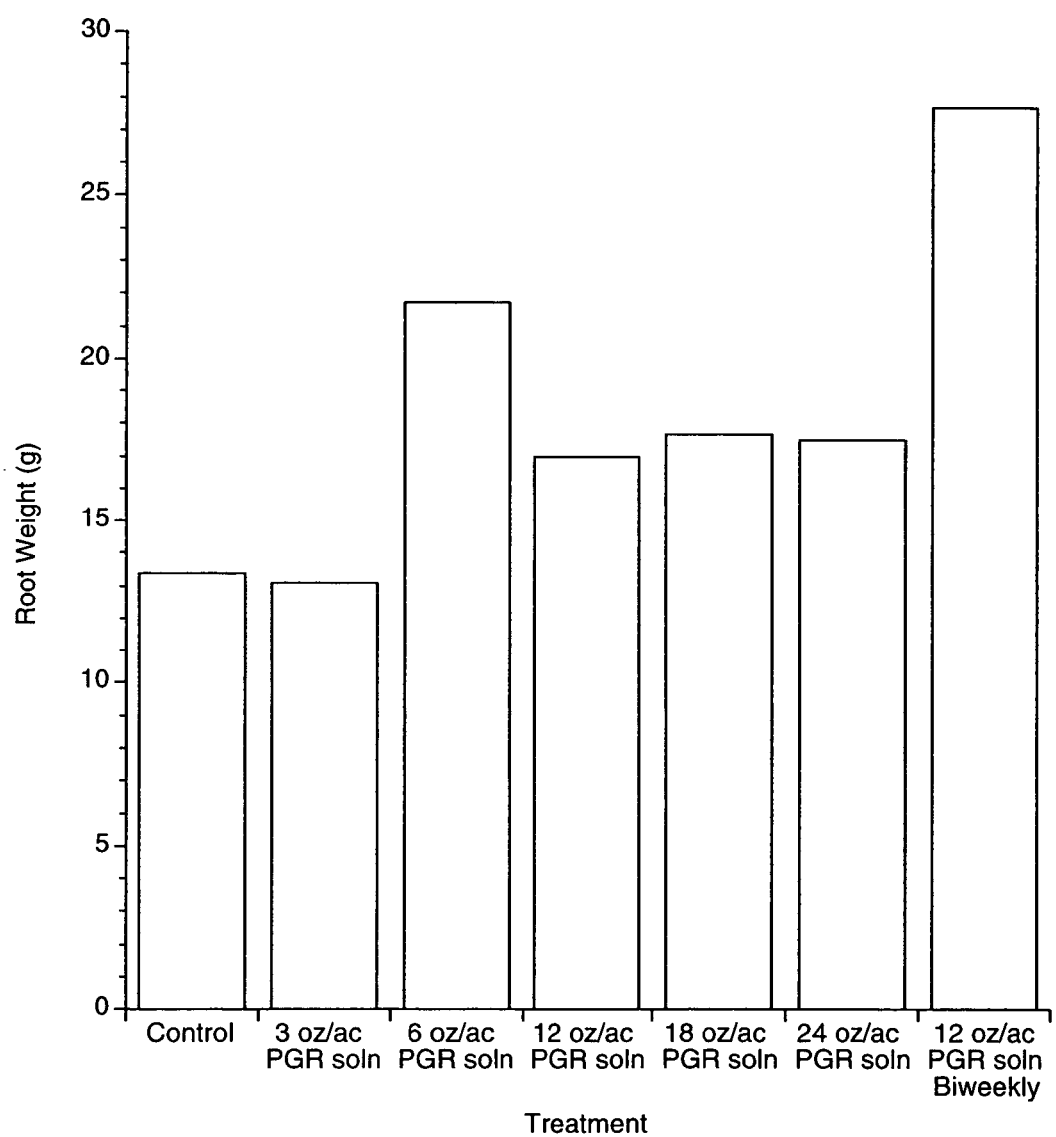

In this experiment, the effects of PGRs on the growth of bell pepper plants were evaluated. Each of four (4) pepper plant replicates were grown outdoors in a field. The plants were grown with a spacing of 12 inches between plants and 42 inches between the rows of plants. Each replicate had fifty (50) plants for each treatment. Five (5) plots of plants were treated once after transplanting with PGR solutions applied at the rates of 3, 6, 12, 18 or 24 oz per acre. A final plot was treated with seven (7) applications of the PGR solution applied bi-weekly beginning after transplanting. The PGR solution had a formulation including 0.015% IAA, 0.005% IBA, 0.009% cytokinin and 0.005% gibberellic acid as the active ingredients. Also present in the solution were 1.000% emulsifier, 0.850% surfactant and 0.050% defoamer. The solutions were applied to the plants from drip lines in two (2) gallons of water per treatment plot for each of the treatments in each of the replicates. Measurements of plant height, canopy diameter and root weight were taken ninety-seven (97) days after transplanting. Plant height in centimeters was measured. Canopy diameter at its widest was measured in centimeters. The weight of the roots in grams was measured after shaking off the soil. The results are reported in Table VI. The effect on plant height, canopy diameter and root weight are illustrated in FIGS. 10a-10c, respectively.

TABLE VI

Effects of PGRs on Pepper Crop Plant Growth

| Treatment | Rate (oz/acre) | Application Frequency | Average Height (cm) | Average Canopy Diameter (cm) | Average Weight (gm) |
|---|---|---|---|---|---|
| Control | 0 | 0 | 29.5 d | 13.6 d | 13.4 e |
| PGR | 3 | 1 | 30.0 d | 16.0 c | 13.1 de |
| PGR | 6 | 1 | 33.2 c | 17.6 bc | 21.7 b |
| PGR | 12 | 1 | 34.3 bc | 18.0 abc | 17.0 cd |
| PGR | 18 | 1 | 33.7 c | 18.1 ab | 17.7 c |
| PGR | 24 | 1 | 36.7 a | 19.0 ab | 17.5 c |
| PGR | 12 | Biweekly | 36.3 ab | 20.0 a | 27.7 a |

Means are different at 5% probability when followed by a different letter.

Application of PGR solutions resulted in increased plant height, canopy diameter and root weight. Plant height and canopy diameter both increased at successively higher rates of application. Plant bushiness was greatest for the PGR treated plants; height was also greater. Root weight was significantly increased with repeated application of the PGR solution. Most PGR treatments had better root growth than the control plants.

EXAMPLE 5

Figure 11A:
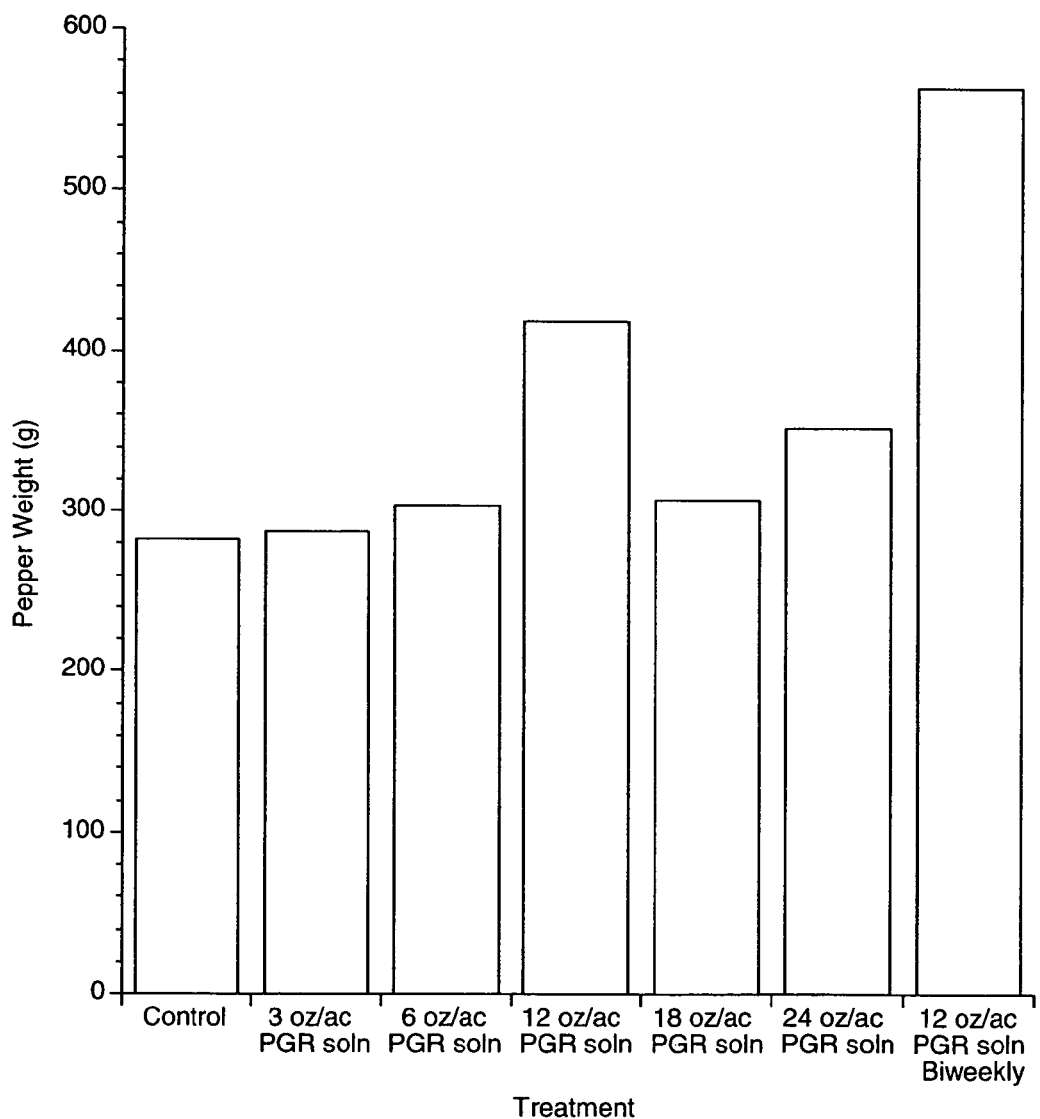
FIGS. 11a and 11b are bar graphs illustrating, respectively, the average yield per plant and percentage of peppers graded large/fancy from pepper plants treated with various dosage rates of a plant growth regulator solution in accord with the present invention as summarized in Table VII.
Figure 11B:
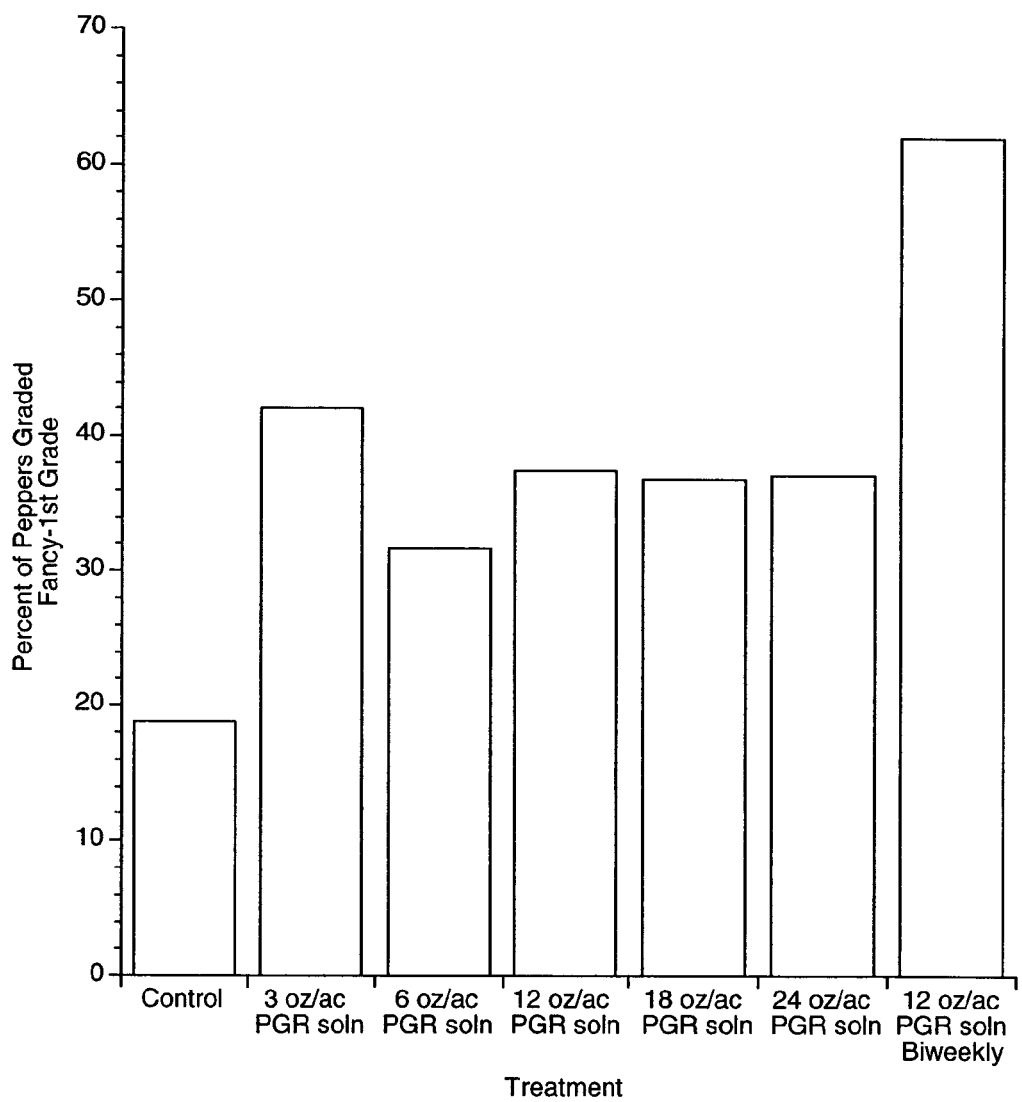

In this experiment, the effects of PGRs on the size and weight of bell peppers were evaluated. Each of four (4) pepper plant replicates were grown outdoors in a field. The plants were grown with a spacing of 12 inches between plants and 42 inches between the rows of plants. Each replicate had fifty (50) plants for each treatment. Five (5) plots of plants were treated once after transplanting with PGR solutions applied at the rates of 3, 6, 12, 18 or 24 oz per acre. A final plot was treated with seven (7) applications of the PGR solution applied bi-weekly beginning after transplanting. The PGR solution had a formulation including 0.015% IAA, 0.005% IBA, 0.009% cytokinin and 0.005% gibberellic acid as the active ingredients. Also present in the solution were 1.000% emulsifier, 0.850% surfactant and 0.050% defoamer. The solutions were applied to the plants from drip lines in two (2) gallons of water per treatment plot for each of the treatments in each of the replicates. Peppers were harvested from all the plants in all of the plots. The number of peppers per plant was recorded. The weights of the harvested peppers were determined. The percentage of large peppers (those graded fancy—first grade) was calculated. The results are recorded in Table VIII. The yield per plant and percentage of large peppers are illustrated in FIGS. 11a and 11b.

TABLE VII

Effects of PGRs on Pepper Crop Harvest

| Treatment | Rate (oz/acre) | Application Frequency | Average Peppers per Plant | Average Yield (gm) | Large Peppers (%) |
|---|---|---|---|---|---|
| Control | 0 | 0 | 3.1 a | 283 b | 19 b |
| PGR | 3 | 1 | 2.8 a | 288 b | 42 ab |
| PGR | 6 | 1 | 2.7 a | 303 b | 32 b |
| PGR | 12 | 1 | 3.3 a | 418 ab | 38 b |
| PGR | 18 | 1 | 2.7 a | 308 b | 37 b |
| PGR | 24 | 1 | 2.9 a | 352 b | 37 b |
| PGR | 12 | Biweekly | 3.6 a | 563 a | 62 a |

Means are different at 5% probability when followed by a different letter.

Though the application of PGR solutions to the pepper plants did not appear to significantly change the number of peppers harvested, it had a marked effect on the size and yield of the peppers. The percentage of peppers classified as large, i.e., fancy—first grade, significantly increased, resulting in a significant increase in the average yield per plant. The largest peppers and the greatest yield were obtained with biweekly application of the PGR solution.

EXAMPLE 6

In this experiment, the effects of PGRs on corn stalk growth were evaluated. Each of four (4) corn plant replicates were grown outdoors in a field. The rows of plants were separated by 42 inches. The plant density was about 30,000 per acre. The plants were treated with 8, 16 or 24 oz/acre of a PGR solution once after seeding of the corn. The PGR solution had the same composition as that used in Example 4. The solutions were applied to the corn from drip lines in 2 gallons of water per treatment plot for each of the treatments in each of the four (4) replicates. The circumference of the stems of ten (10) plants from each treatment in each of the four (4) replications were measured forty-eight (48) days after planting. The results are reported in Table VIII.

TABLE VIII

Effects of PGRs on Field Corn Stalk Circumference

| Treatment | Rate (oz/acre) | Application Frequency | Average Stalk Circumference (mm) |
|---|---|---|---|
| Control | 0 | 0 | 75.3 ± 3.0 |
| PGR | 8 | 1 | 79.9 ± 2.1 |
| PGR | 16 | 1 | 79.4 ± 0.8 |
| PGR | 24 | 1 | 77.3 ± 3.2 |

Means are different at 5% probability when followed by a different letter.

Corn stem circumference increased with increasing concentration of the applied PGR solution. A maximum response was reached at the 16 oz/acre rate and then decreased slightly at higher rate.

EXAMPLE 7

The effects of PGRs on the growth and yield of bell pepper plants were evaluated in this experiment. The experiment employed a randomized (4) replicate trial. The bell peppers were planted 12 inches apart in 2 rows with 40 inches between rows. The PGR solution had the same composition as that used in Example 4. Controls were merely treated with water. The solutions were applied to the plants at the rate of 6 or 12 oz per acre from drip lines. The PGR solutions were applied shortly after transplanting as a single treatment or on a repeated bi-weekly basis as indicated in Table IX. The plant height and canopy width were measured at maturity. Peppers were harvested from all of the plants in all of the plots. The weights of the harvested peppers were determined. The percentage of larger peppers (those graded fancy—first grade) was calculated. The weight of the plant roots were determined after harvest. The results are reported in Table IX

TABLE IX

Bell Pepper Crop Performance with PGR

| Treatment | Plant Height (cm) | Canopy Width (cm) | Root Weight (g) | Fruit Wgt Ave. (g) | Fancy (%) |
|---|---|---|---|---|---|
| Control | 30 d | 13.6 d | 13.4 e | 283 b | 37 c |
| PGR (once 6 oz/acre) | 33 c | 17.6 bc | 21.7 b | 303 b | 52 bc |
| PGR (once 12 oz/acre) | 34 bc | 18 abc | 17.0 cd | 418 ab | 62 ab |
| PGR (bi-weekly - 12 oz/acre) | 36 ab | 20 a | 27.7 a | 563 a | 77 a |

Means followed by a different letter are different at p = 0.05 (LSD).

Treatment with PGR results in larger plants with significantly larger root growth. Both the average weight of the harvested peppers and the percentage of peppers graded fancy are dramatically increased, doubling with bi-weekly application in comparison to the control.

EXAMPLE 8

The effect of PGRs on onion yield was examined in this experiment. This experiment employed a randomized (4) replicate trial. Onions were sown in rows in 50 foot plots. The rows were 40 inches apart. Normal production practices were used in the trial. The PGR solution had the same composition as that used in Example 4. Controls were merely treated with water. The PGR solutions were applied at the rate of 6 or 12 oz per acre from drip lines on a weekly basis throughout the growing season.

TABLE X

Onion Crop Performance with PGR

| Treatment | Rate (oz/acre) | Large Onions (Bags per acre) | Total Onions (Bags per acre) |
|---|---|---|---|
| Control | 0 | 370 | 551 |
| PGR | 6 | 499 | 635 |
| PGR | 12 | 698 | 819 |

Both the total yield and the yield of larger onions were significantly increased by the application of PGR solutions on a weekly basis. As expected, both yields showed the greatest improvement when applied at the higher rate of 12 oz per acre.

EXAMPLE 9

The effect of PGRs on the yield and grade of potatoes was evaluated in this experiment. Potatoes were planted in 40 foot rows with a spacing of 36 inches between rows. Treatments were replicated 5 times. Normal production practices were followed. The PGR solution used in this experiment comprised an aqueous solution containing 0.015% IAA, 0.005% IBA, 0.009% cytokinin, 0.005% gibberellic acid, 1.000% emulsifier, 0.850% surfactant and 0.050% defoamer, together with 8.0% boron and 0.004% molybdenum. The PGR solutions were applied at the rate of 0.5 or 1.0 gallon per acre as a side dressing at the last cultivation between the rows. The potatoes were harvested, weighed and graded. The results, including both total yield (lbs per plant) and yield of USA grade No. 1 potatoes per plant, are reported in Table XI.

TABLE XI

Effect of PGR/B/Mo on Potato Crop Performance

| Treatment | Yield (lb/plant) | Difference % from Control | USA No. 1 potatoes Number per Plant | Difference % from Control |
|---|---|---|---|---|
| Control | 11.0 ± 0.4 | | 10.4 | |
| PGR/B/Mo 0.5 gal/acre | 11.5 ± 0.6 | 4.6% | 11.2 ± 1.4 | 7.7% |
| PGR/B/Mo 1 gal/acre | 14.1 ± 0 | 28.3% | 14.4 ± 4.1 | 38.5% |

Means are represented with their standard deviations.

Treatment with PGR/B/Mo solutions resulted in both improved total yield and yield of grade No. 1 potatoes. At the higher application rate, the total yield is increased by more than 28%, while the yield of grade No. 1 potatoes is improved by more than 38%.

EXAMPLE 10

The effect of PGRs added together with conventional plant nutrients on the yield and grade of potatoes was evaluated in this experiment. Potatoes were planted in 40 foot rows with a spacing of 36 inches between rows. Treatments were replicated 5 times. Normal production practices were followed. The PGR solution used in this experiment comprised an aqueous solution containing 0.015% IAA, 0.005% IBA, 0.009% kinetin, 0.005% gibberellic acid, 1.000% emulsifier, 0.850% surfactant and 0.050% defoamer, together with a compliment of nutrients. The treatments were applied at the rate of one gallon per acre via side dressing at the last cultivation between the rows. The treatments were applied either on a weekly or bi-weekly basis as indicated in Table XII. The potatoes were harvested, weighed and graded. The results, including both total yield (lbs per plant) and yield of USA grade No. 1 potatoes per plant, are reported in Table XII.

TABLE XII

Effect of PGR/Nutrient on potato crop performance

| Treatment | Yield (lb/plant) | Difference % from Control | USA No. 1 potatoes Number per Plant | Difference % from Control |
|---|---|---|---|---|
| Control | 11.0 ± 0.4 | | 10.4 | |
| PGR/Nutrient (weekly) | 12.8 ± 0.6 | 16.4% | 16.4 ± 4.1 | 61.5% |
| PGR/Nutrient (bi-weekly) | 15.6 ± 1.8 | 42.0% | 14.6 ± 1.8 | 40.4% |

Means are represented with their standard deviations.

Treatment with both PGRs and nutrients produced both improved total yield and yield of grade No. 1 potatoes. Total yield significantly increased both bi-weekly application, while the yield of grade No. 1 potatoes significantly increased with either application.

The foregoing description of the invention has been directed in primary part to particularly preferred embodiments in accord with the requirements of the Patent Statue and for purposes of explanation and illustration. It will be apparent, however, to those skilled in the art that many modifications and changes in the specifically described methods and compositions may be made without departing from the true scope and spirit of the invention. For example, while indole-3-acetic acid is the preferred auxin, synthetic auxins, specifically, indole-3-butyric acid, may be employed. Further, other plant growth regulators, particularly cytokinins or gibberellins, may be used to manipulate the auxin levels. Further, while preferred application rates have been presented, it is known that different plant species and, in fact, different tissues within a given plant all require different auxin levels. Thus, those skilled in the art may readily adjust the suggested application rates as required to achieve the desired results. Further, while Applicant has attempted to explain the reasons for the observed improvements in plant architecture, growth and crop yield, Applicant does not wish to be held to the theory proposed, because that mechanism is not fully understood. Therefore, the invention is not restricted to the preferred embodiments described and illustrated herein, but covers all modifications which may fall within the scope of the following claims.

What is claimed is:

1. A plant growth regulating solution comprising,
an aqueous solution with
0.015% indole-3-acetic acid,
0.005% indole-3-butyric acid,
0.009% cytokinin, and
0.005% gibberellic acid, as active ingredients.

2. The plant growth regulating solution of claim 1 further comprising,
1.000% emulsifier,
0.850% surfactant, and
0.050% defoamer, as inactive ingredients.

3. A method for increasing the weight of fruit in tomato plants comprising the steps of,
forming a plant growth regulating solution of 0.42 micrograms indole-3-acetic acid, 0.42 micrograms kinetin, and water;
applying the growth regulating solution to the foliage of tomato plants, or to the soil in which tomato plants are growing, at a rate of 6 oz/acre.

4. The method of claim 3, wherein
the plant growth regulating solution includes 100 ml of water, and
the plant growth regulating solution is applied to the soil in which tomato plants are growing at a rate of 6 oz/acre.

5. The method of claim 3, wherein
the plant growth regulating solution includes 50 ml of water; and
the plant growth regulating solution is applied to the foliage of tomato plants at a rate of 6 oz/acre.

6. A method for increasing internode length in cucumber plants comprising the steps of,
forming an aqueous solution with 0.015% indole-3-acetic acid, 0.005% indole-3-butyric acid, 0.009% cytokinin, and 0.005% gibberellic acid,
adding 0.0042 ml of the aqueous solution to 100 ml of water to form a diluted solution, and
applying the diluted solution to the soil in which cucumber plants are growing at the time of planting, and weekly thereafter, at a rate of 6 oz/acre.

7. A method for increasing at least one of the yield, plant height, canopy diameter, and root weight of bell pepper plants comprising the steps of,
   forming an aqueous solution with 0.015% indole-3-acetic acid, 0.005% indole-3-butyric acid, 0.009% cytokinin, and 0.005% gibberellic acid,
   adding 0.0042 ml of the aqueous solution to 100 ml of water to form a diluted solution, and
   applying the diluted solution to the soil in which the bell pepper plants are growing.

8. The method of claim 7 wherein
   the diluted solution is applied to the soil in which the bell pepper plants are growing at a rate of 12 oz/acre on a biweekly basis.

9. A method for increasing the size of the stalks of corn plants comprising the steps of,
   forming an aqueous solution with 0.015% indole-3-acetic acid, 0.005% indole-3-butyric acid, 0.009% cytokinin, and 0.005% gibberellic acid,
   adding 0.0042 ml of the aqueous solution to 100 ml of water to form a diluted solution, and
   applying the diluted solution to the soil in which the corn plants are growing.

10. The method of claim 9, wherein
    the diluted solution is applied to the soil in which the corn plants are growing once at a rate of 8 oz/acre after seeding.

11. A method for increasing the yield of onion plants comprising the steps of,
    forming an aqueous solution with 0.015% indole-3-acetic acid, 0.005% indole-3-butyric acid, 0.009% cytokinin, and 0.005% gibberellic acid,
    adding 0.0042 ml of the aqueous solution to 100 ml of water to form a diluted solution, and
    applying the diluted solution to the soil in which the onion plants are growing.

12. The method of claim 11 wherein
    the diluted solution is applied to the soil in which the onion plants are growing at a rate of 12 oz/acre on a weekly basis.

13. A method for increasing the yield and grade of potato plants comprising the steps of,
    forming an aqueous solution with 0.015% indole-3-acetic acid, 0.005% indole-3-butyric acid, 0.009% cytokinin, and 0.005% gibberellic acid,
    adding 0.0042 ml of the aqueous solution into 100 ml of water to form a diluted solution, and
    applying the diluted solution to the soil in which the potato plants are growing.

14. The method of claim 13 wherein
    the diluted solution is applied at a rate of 1.0 gal/acre as a side dressing at the last cultivation between rows of potato plants.

15. The method of claim 13 wherein
    the diluted solution is applied at a rate of 1.0 gal/acre as a side dressing at the last cultivation between rows of potato plants, and on a weekly or bi-weekly basis thereafter.

16. The method of claim 13 wherein
    the aqueous solution further comprises 8.0% boron.

* * * * *

UNITED STATES PATENT AND TRADEMARK OFFICE
CERTIFICATE OF CORRECTION

PATENT NO. : 8,207,091 B2  
APPLICATION NO. : 10/920487  
DATED : June 26, 2012  
INVENTOR(S) : Jerry H. Stoller, Sherry Leclere and Albert Liptay Page 1 of 1

It is certified that error appears in the above-identified patent and that said Letters Patent is hereby corrected as shown below:

Please amend title page of application to include:

"Related U.S. Application Data

Item (60) Provisional application No. 60/549,486, filed on March 2, 2004."

Signed and Sealed this
Eighteenth Day of November, 2014

Michelle K. Lee
*Deputy Director of the United States Patent and Trademark Office*